(12) United States Patent
Duran Lopez et al.

(10) Patent No.: US 8,440,861 B2
(45) Date of Patent: May 14, 2013

(54) SOLID FORMS OF AN N-(PHENYLMETHYL)PROPANAMIDE DERIVATIVE AND PROCESSES OF PREPARATION

(75) Inventors: Ernesto Duran Lopez, Castellbisbal (ES); Monica Benito Velez, L'Hospitalet de Llobregat (ES); Jordi Bosch i Lladó, Girona (ES)

(73) Assignee: Medichem, S.A., Sant Joan Despi (ES)

( * ) Notice: Subject to any disclaimer, the term of this patent is extended or adjusted under 35 U.S.C. 154(b) by 235 days.

(21) Appl. No.: 12/851,015

(22) Filed: Aug. 5, 2010

(65) Prior Publication Data

US 2011/0034731 A1  Feb. 10, 2011

Related U.S. Application Data

(60) Provisional application No. 61/231,936, filed on Aug. 6, 2009, provisional application No. 61/231,932, filed on Aug. 6, 2009.

(51) Int. Cl.
*C07C 233/04* (2006.01)

(52) U.S. Cl.
USPC .......................................... 564/158; 514/616

(58) Field of Classification Search .................. 564/216, 564/219, 223, 158; 514/629, 616
See application file for complete search history.

(56) References Cited

U.S. PATENT DOCUMENTS

| | | | |
|---|---|---|---|
| 5,773,475 A * | 6/1998 | Kohn ............................. | 514/616 |
| 6,048,899 A | 4/2000 | Kohn et al. | |
| 2008/0027137 A1 | 1/2008 | Riedner et al. | |
| 2009/0143472 A1 * | 6/2009 | Madhra et al. ................ | 514/616 |
| 2009/0298947 A1 * | 12/2009 | Mundorfer et al. ........... | 514/616 |

FOREIGN PATENT DOCUMENTS

| | | |
|---|---|---|
| EP | 2 067 765 A2 | 6/2009 |
| EP | 1 799 635 B1 | 2/2010 |
| EP | 2462107 | 6/2012 |
| WO | WO 97/33861 A1 | 9/1997 |
| WO | WO 2006/037574 A1 | 4/2006 |
| WO | WO 2009/146325 A1 | 12/2009 |
| WO | WO 2010/052011 A1 | 5/2010 |
| WO | WO 2010/060624 A2 | 6/2010 |
| WO | WO 2011/015617 A1 | 2/2011 |

OTHER PUBLICATIONS

Dolberg et al., "Lacosamide (CAS RN=175481-36-4 Diffraction Pattern," Sep. 1, 2009.
Center for Drug Evaluation & Research: Environmental Assessment—Application No. NDA 22-253 & 22-254 (2008).
J. Jacques et al., Krieger Publishing Company, 1991, p. 53.
Kinbara et al., *J. Am. Chem. Soc.*, 118, 3441-3449 (1996).

* cited by examiner

*Primary Examiner* — Shailendra Kumar
(74) *Attorney, Agent, or Firm* — Leydig, Voit & Mayer, Ltd.

(57) ABSTRACT

The invention relates to solid forms of the anti-epileptic agent lacosamide (I). The invention also relates to mixtures of solid forms of lacosamide. The invention further relates to mixtures of lacosamide enantiomers crystallized in a conglomerate Form and the use thereof in providing enantiomerically enriched lacosamide, preferably lacosamide enriched with the (R)-enantiomer of lacosamide.

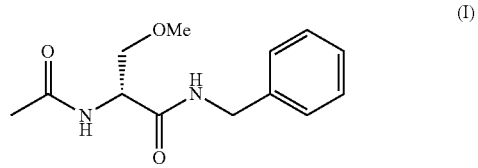

(I)

17 Claims, 13 Drawing Sheets

SOLID FORMS OF AN N-(PHENYLMETHYL)PROPANAMIDE DERIVATIVE AND PROCESSES OF PREPARATION

CROSS-REFERENCE TO RELATED APPLICATIONS

This patent application claims the benefit of U.S. Provisional Patent Application No. 61/231,932, filed Aug. 6, 2009, and U.S. Provisional Patent Application No. 61/231,936, filed Aug. 6, 2009, both of which are incorporated by reference.

BACKGROUND OF THE INVENTION

Lacosamide (Compound I) is the international commonly accepted name for (2R)-2-(acetylamino)-3-methoxy-N-(phenylmethyl)propanamide (which is also known as (R)-N-benzyl-2-acetamido-3-methoxypropionamide), and has an empirical formula of $C_{13}H_{18}N_2O_3$ and a molecular weight of 250.30 g/mol.

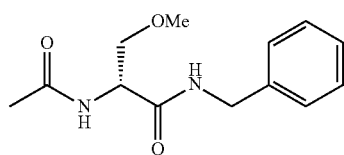

(I)

Lacosamide is an active substance indicated for adjunctive treatment of partial-onset seizures and diabetic neuropathic pain. In the United States, lacosamide is marketed under the name VIMPAT™ for the treatment of epilepsy.

Examples 1 and 2(b) of U.S. Pat. No. 5,773,475 disclose the isolation of lacosamide after evaporation from acetonitrile and filtration or trituration with diethyl ether. Lacosamide was obtained substantially enantiomerically pure, as defined therein, as was ascertained by the addition of excess (R)-(–)-mandelic acid to a $CDCl_3$ solution of lacosamide, which gave only one signal for the acetyl methyl and ether methyl protons. In Example 5 of U.S. Pat. No. 5,773,475, lacosamide was prepared from D-serine and was purified by flash chromatography to obtain lacosamide as the (R)-enantiomer, but no mention was made regarding its enantiomeric purity. U.S. Pat. No. 5,773,475 generally indicates that the optical purity of lacosamide may be enhanced by further separation of the (S)-enantiomer from the (R)-enantiomer, by standard techniques known in the art, such as chiral chromatography using a standard chiral support known in the art. U.S. Pat. No. 5,773,475 further reports the melting point of the thus obtained solid lacosamide as 143-144° C. However, it does not report whether the solid is crystalline.

The continuation-in-part of U.S. Pat. Nos. 5,773,475, 6,048,899 discloses two examples for the preparation of lacosamide. Example 1 of U.S. Pat. No. 6,048,899 corresponds to Example 5 of parent U.S. Pat. No. 5,773,475. However, Example 1 of U.S. Pat. No. 6,048,899 indicates that lacosamide is obtained as an approximate 85:15 mixture of the (R)- and (S)-enantiomers respectively. In Example 2 of U.S. Pat. No. 6,048,899, lacosamide is obtained substantially enantiomerically pure, as defined therein, as was ascertained by the addition of excess (R)-(–)-mandelic acid to a $CDCl_3$ solution of lacosamide. However, it does not report whether the solid is crystalline.

European Patent Application No. 1799635A1 relates to lacosamide preparation wherein the methylation step is carried out using dimethylsulphate and either n-butyl lithium or aqueous sodium hydroxide and phase transfer catalysis. EP 1799635A1 indicates that the removal of the (S)-enantiomer during production of lacosamide is extremely difficult. The methylation step using dimethylsulphate is described to be advantageous since it does not result in any racemization of the lacosamide product. However, the use of dimethylsulphate, which is a strong, highly toxic methylating agent, may lead to safety and environmental issues when producing lacosamide on a large scale. Furthermore, the use of n-butyl lithium at industrial scale is undesired since n-butane, a highly flammable gas, is obtained as a by-product of the reaction. On the other hand, phase transfer catalysts are expensive reagents which are difficult to be removed due to their high solubility in both water and organic solvents. Example 3 describes that the lacosamide product was crystallized by cooling a solution in ethyl acetate and the thus isolated lacosamide was obtained with a chiral purity of 99.8% e.e. However, EP 1799635A1 does not report any physical properties for the obtained lacosamide.

European Patent Application No. 2067765A2 relates to lacosamide preparation wherein N-trityl-D-serine is used as a starting material in order to minimize racemization due to the use of the trityl bulky protecting group, thus providing lacosamide substantially free of the (S)-enantiomer. However, such a process suffers from drawbacks, including for example the potential cost associated with the use of the above mentioned D-serine starting material and furthermore the N-protection/N-deprotection steps of the amine moiety also being potentially associated with cost and productivity issues for the overall process when used on an industrial scale. Concretely, the use of N-trityl protecting group is particularly detrimental due to the very low atom efficiency of this process, since the molecular weight of the N-trityl protecting group (243.33 g/mol) is comparable to the molecular weight of lacosamide (250.30 g/mol). EP 2067765A2 also specifically describes the isolation of lacosamide after evaporation from dichloromethane or ethyl acetate and reports a melting point of 142-143° C. and a chiral purity by HPLC between 99.98 and 100%. The isolated lacosamide is said to be recrystallized in toluene or ethyl acetate. However, EP 2067765A2 does not report physical properties for the obtained lacosamide.

PCT Patent Application No. WO 2010/052011 describes different processes for the manufacture of optically enriched lacosamide. One of the processes relates to the preparation of lacosamide as a mixture of enantiomers which is thereafter separated by chiral chromatographic separation into its different enantiomers. Another process relates to the resolution of the lacosamide intermediate 2-amino-N-benzyl-3-methoxypropionamide by diastereomeric salt formation or chiral chromatographic separation followed by acetylation and crystallization of the obtained lacosamide. However, such chiral chromatographic separation techniques are costly processes. Also resolution of an enantiomeric mixture by diastereomeric salt formation requires adequate chiral resolving agent available in an optically pure form, which can be both difficult and expensive, and furthermore requires recovery of the chiral resolving agent in high yield.

PCT Patent Application No. WO 2009/146325 describes polymorphic Forms I, II and III and an amorphous Form of lacosamide and processes for the preparation thereof. According to WO 2009/146325 the crude lacosamide used as starting material in the Examples is prepared by known methods such as those described in U.S. Pat. No. 6,048,899 and U.S. Patent Application No. 2008/0027137 (the latter is the U.S. equivalent to above discussed EP 1799635A1). No mention is made regarding the enantiomeric purity of lacosamide as prepared in accordance with WO 2009/146325.

PCT Patent Application No. WO 2010/060624 discloses polymorphic Forms R, S and T of lacosamide and processes for the preparation thereof. According to WO 2010/060624 the crude lacosamide used in the Examples as starting material is prepared by methods described in WO 97/033861, which is equivalent to above discussed U.S. Pat. Nos. 5,773, 475 and 6,048,899. No mention is made regarding the enantiomeric purity of lacosamide as prepared in accordance with WO 2010/060624.

IPCOM 000187362D discloses a crystalline Form of lacosamide characterized by X-ray diffraction and prepared by recrystallization from 2-propanol at 50° C.

Polymorphism is defined as the ability of a substance to exist in two or more crystalline phases that have a different arrangement and/or conformation of the molecules in the crystal lattice. Polymorphs typically differ in their physical properties such as, for example, melting point, solubility, and chemical reactivity. Thus, the particular characteristics of the respective polymorphs can appreciably influence the solubility profile of a chemical substance, such as the dissolution rate. Further, the particular characteristics of the respective polymorphs can appreciably influence pharmaceutical properties such us dissolution rate and bioavailability.

Crystalline solids can often require a significant amount of energy for dissolution due to their highly organized lattice like structures. For example, the energy required for dissolution of a drug molecule from a crystal lattice can be much higher than the energy required for dissolution from an amorphous Form.

Amorphous Forms of drugs can exhibit different solubility properties compared to crystal Forms, and in some instances amorphous pharmaceuticals can be markedly more soluble than their crystalline counterparts [Hancock B. C., *Pharm. Res.*, 17(4), 397 2000]. Additionally, amorphous drugs can exhibit different bioavailability patterns, as compared to their crystalline Form. For some therapeutic indications, a particular bioavailability pattern may be favored with respect to another. Therefore, it is often desirable to have amorphous Forms of drugs and processes for their preparation.

There is an ongoing need for new and improved polymorphic Forms of existing drug molecules for improved drug formulation. For example, new and improved polymorphic Forms having desirable bioavailability and/or improved stability, are continually being sought.

In view of the aforementioned, there is a desire to identify and isolate various solid Forms of lacosamide that can be desirable for pharmaceutical formulation. Further, there is a desire to have a reliable and cost efficient process for producing lacosamide in one or more of its solid Forms and also with desirable enantiomeric purity.

BRIEF SUMMARY OF THE INVENTION

The invention is concerned with lacosamide, solid Forms of lacosamide, and processes of preparing lacosamide. Furthermore, the present invention is concerned with processes for increasing the enantiomeric excess of lacosamide.

The present invention provides novel crystalline Form III of lacosamide as characterized herein, an amorphous Form of lacosamide as characterized herein and also mixtures based on the above. The present invention also provides processes for preparing crystalline and amorphous Forms of lacosamide as described herein and pharmaceutical compositions comprising novel crystalline and amorphous Forms of lacosamide and/or mixtures thereof as characterized herein. The present invention also provides mixtures of lacosamide enantiomers crystallized in a conglomerate Form, and the use thereof to preferably provide lacosamide enantiomerically enriched in the (R)-enantiomer.

The invention also provides a process for preparing enantiomerically enriched lacosamide.

The invention also provides a process for increasing the enantiomeric excesss of enantiomerically enriched lacosamide.

DETAILED DESCRIPTION OF THE INVENTION

Applicants have now identified novel crystalline and amorphous Forms of lacosamide as characterized herein. Furthermore, the applicants also provide mixtures of lacosamide crystalline and/or substantially amorphous Forms of lacosamide again as characterized herein.

Figure 1:
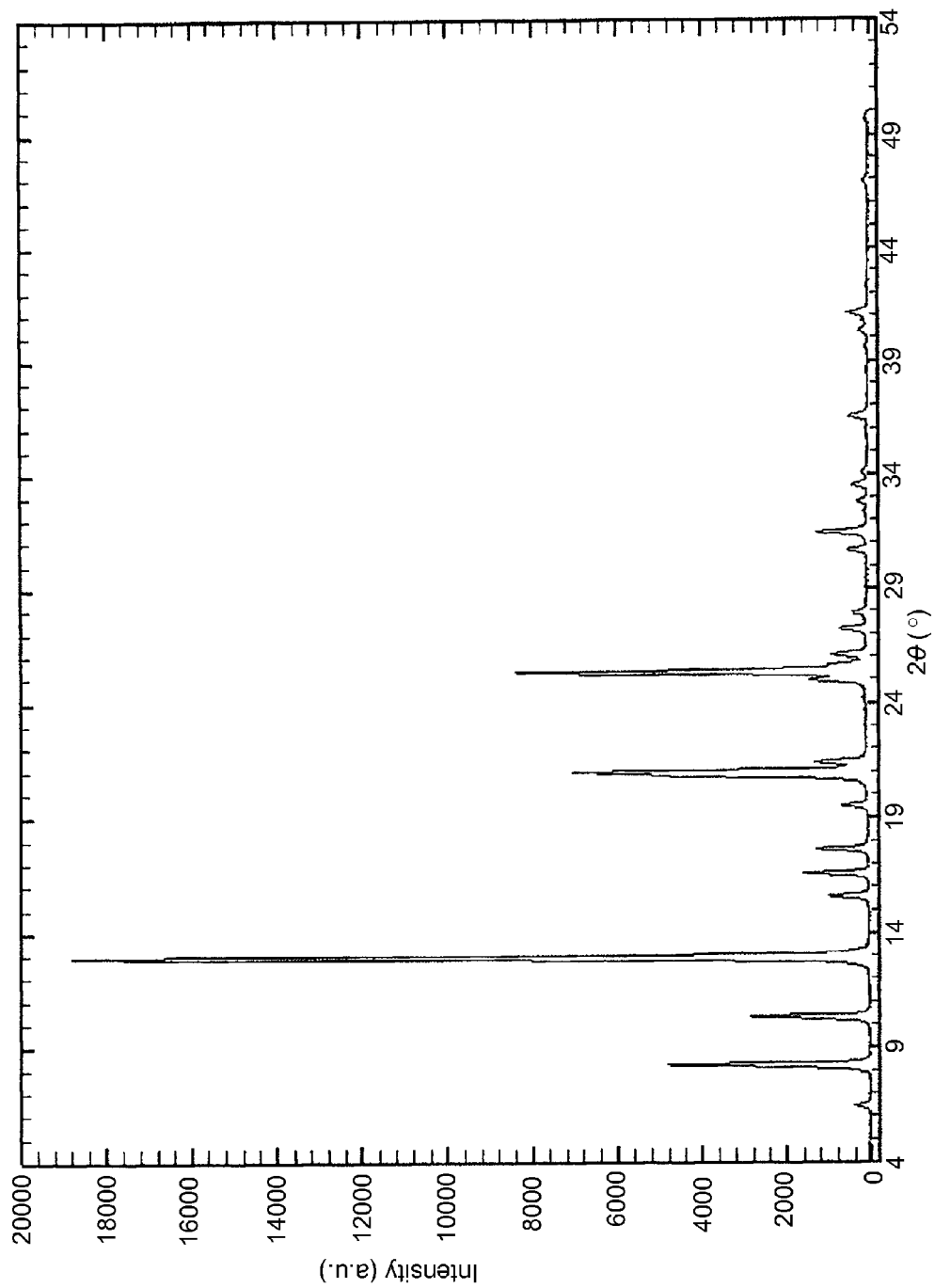
FIG. 1 depicts the X-ray powder diffractogram (XRD) of lacosamide crystalline Form I.

Lacosamide crystalline Form I can be characterized by an XRD pattern comprising peaks (2θ) at 8.2, 10.3, 12.9, 15.6, 16.6, 17.6, 19.5, 20.8, 21.0, 21.4, 25.0, 25.3, 26.1, 27.2, 30.7, 31.4, and 36.6 degrees (±0.2 degrees). FIG. 1 depicts the XRD of lacosamide crystalline Form I.

Figure 2:
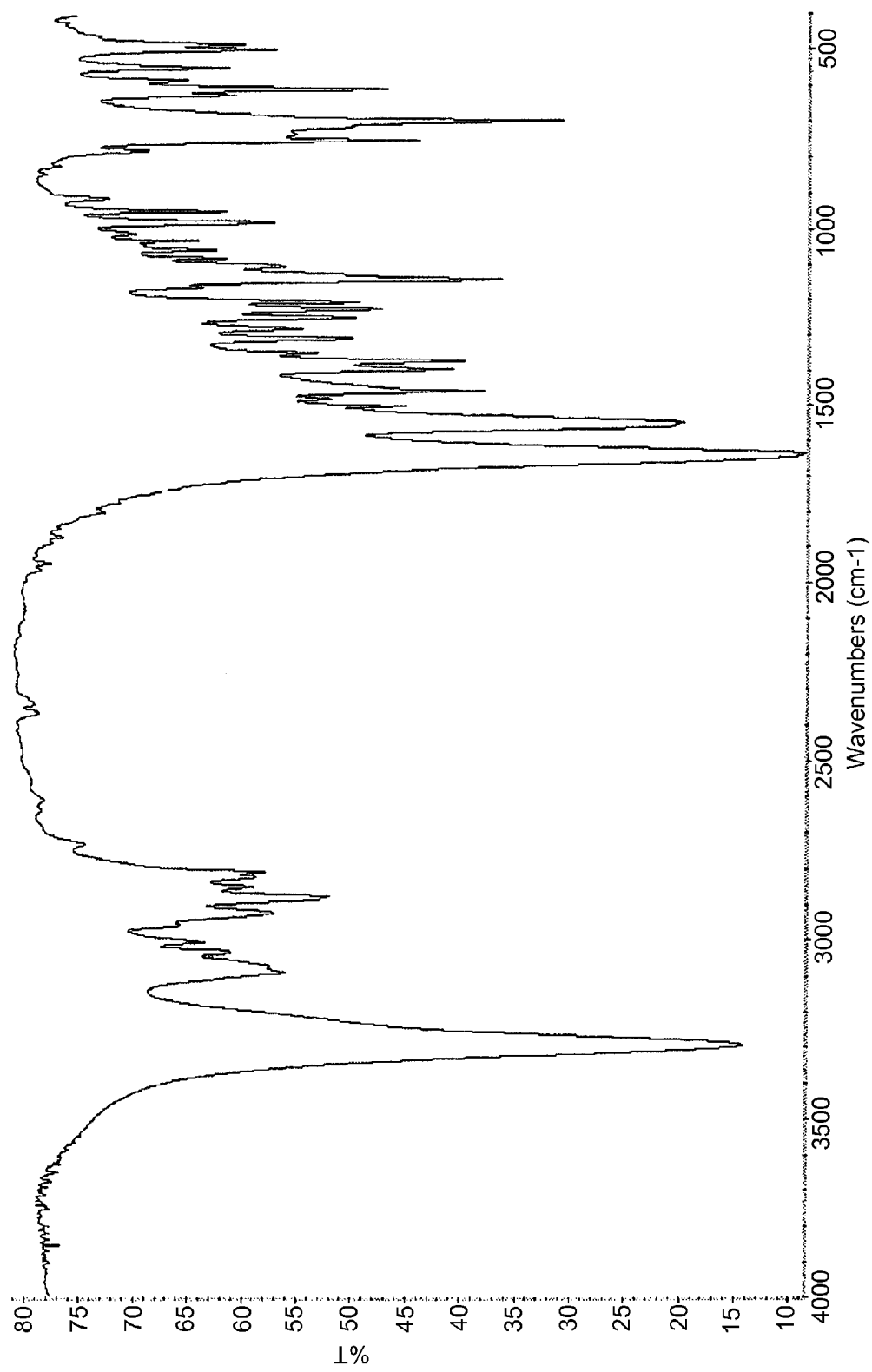
FIG. 2 depicts the Infrared (IR) spectrum of lacosamide crystalline Form I.

Lacosamide crystalline Form I can also be characterized by an IR spectrum comprising characteristic absorption bands at: 3289, 3088, 3033, 3005, 2923, 2880, 2848, 2806, 1639, 1545, 1454, 1370, 1305, 1245, 1197, 1136, 1103, 977, 944, 912, 748, 695, 603, 545, and 494 $cm^{-1}$. FIG. 2 depicts the IR spectrum of lacosamide crystalline Form I.

Figure 3:
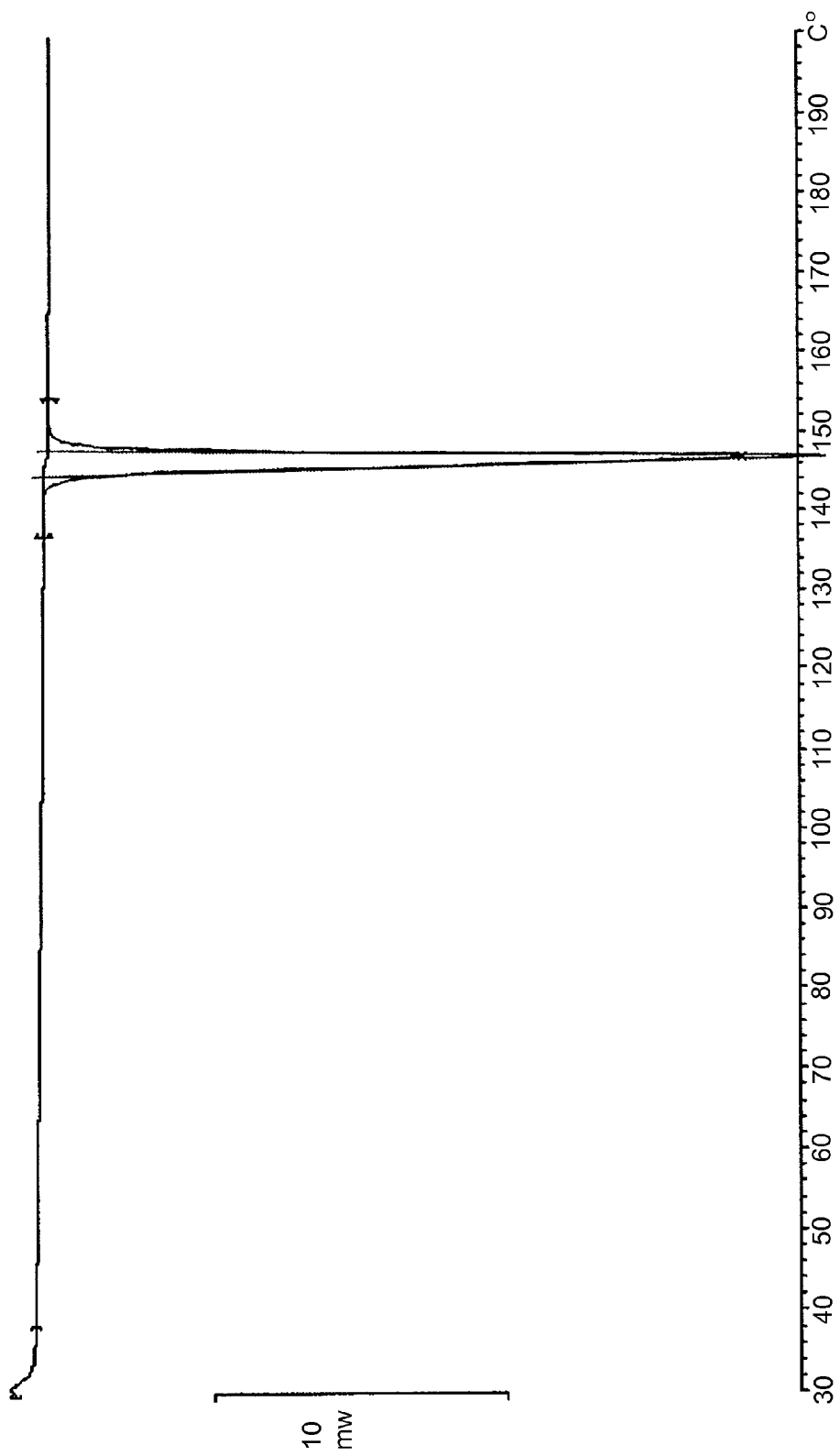
FIG. 3 depicts the DSC of lacosamide crystalline Form I.

Lacosamide crystalline Form I can also be characterized by a melting point of about 144.8° C. (onset temperature) and about 145.6° C. (peak temperature) as measured by DSC. FIG. 3 depicts the DSC plot of lacosamide crystalline Form I.

Lacosamide crystalline Form I corresponds to an anhydrous, non-solvated crystalline form, and therefore no weight loss is observed by thermogravimetric analysis below the melting point.

Lacosamide crystalline Form I can be prepared by crystallizing lacosamide in a solvent at room temperature or at reflux temperature of the solvent. Suitable solvents include but are not limited to alcohols, such as, for example, methanol, ethanol, 2-butanol and 1-pentanol, alkoxyalcohols such as 2-ethoxyethanol, ketones such as, for example, acetone, methyl isobutyl ketone, and cyclopentanone, halogenated solvents such as, for example, chloroform, ethers such as, for example, methyl tert-butyl ether, tetrahydrofuran, and 1,3-dioxolane, alkanes such as methyl cyclohexane, and esters such as, for example, isobutyl acetate.

Alternatively, lacosamide crystalline Form I can be prepared by suspending lacosamide in a suitable solvent at room temperature or reflux temperature of the solvent. Suitable solvents include but are not limited to n-butyl acetate or heptane.

Lacosamide crystalline Form I can also be prepared by suspending lacosamide in water at room temperature for two days.

Lacosamide crystalline Form I can also be prepared by dissolving lacosamide in a suitable solvent at room temperature or reflux temperature of the solvent, and then adding heptane or methyl tert-butyl ether (MTBE) as antisolvent, thereby precipitating lacosamide crystalline Faun I from solution. Suitable solvents include but are not limited to acetone, tetrahydrofuran, 1,4-dioxane, toluene, acetonitrile, 2-propanol and chloroform.

Figure 4:
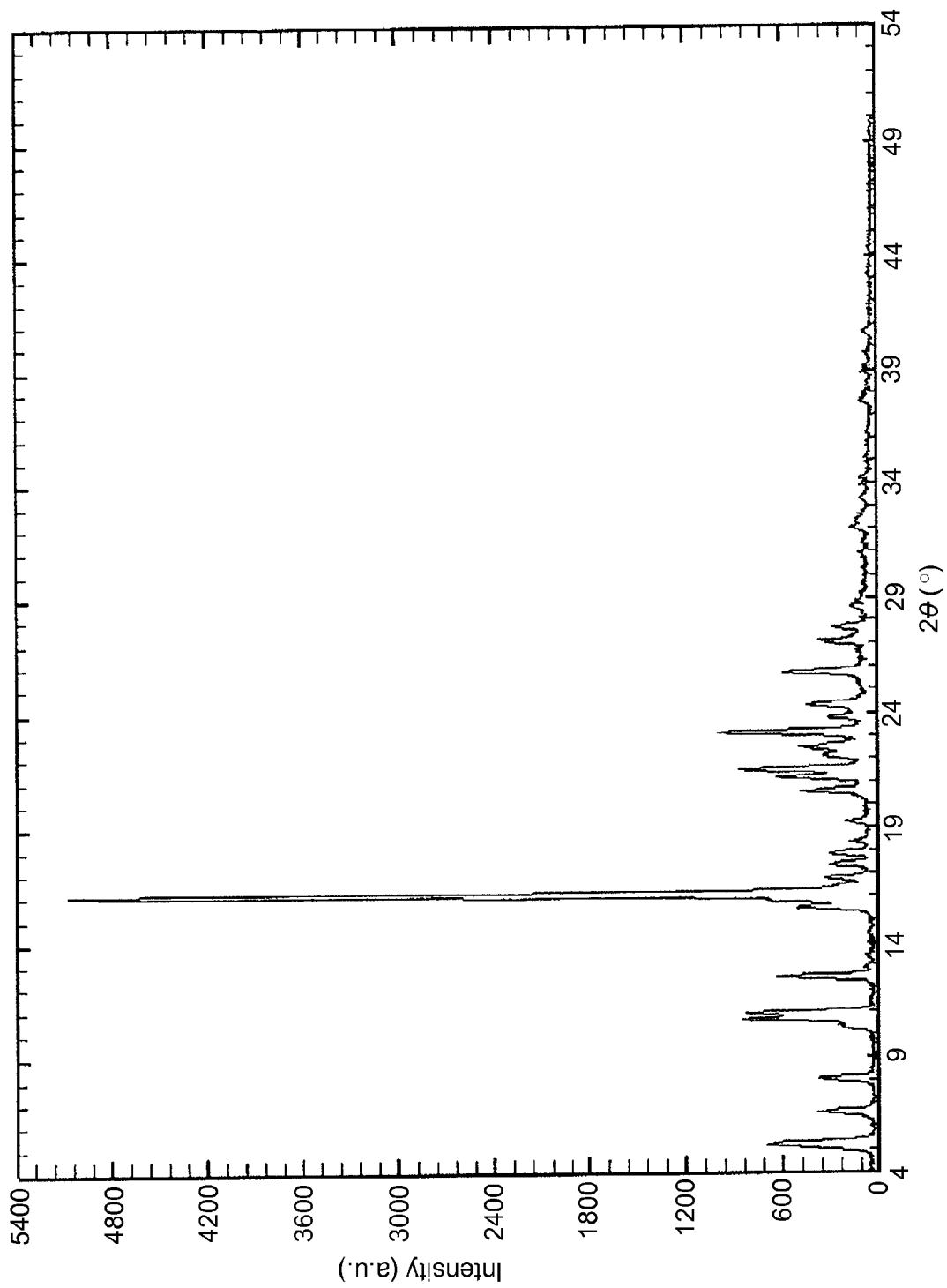
FIG. 4 depicts the X-ray powder diffractogram (XRD) of lacosamide crystalline Form II.

Lacosamide crystalline Form II can be characterized by an XRD pattern comprising peaks (2θ) at 5.2, 6.6, 8.1, 10.6, 10.9, 12.5, 15.5, 16.1, 16.8, 17.4, 17.8, 20.5, 21.2, 21.5, 22.1, 22.5, 23.1, 23.8, 24.3, 25.7, 27.1, and 27.6 degrees (±0.2 degrees). FIG. 4 depicts the XRD of lacosamide crystalline Form II.

Figure 5:
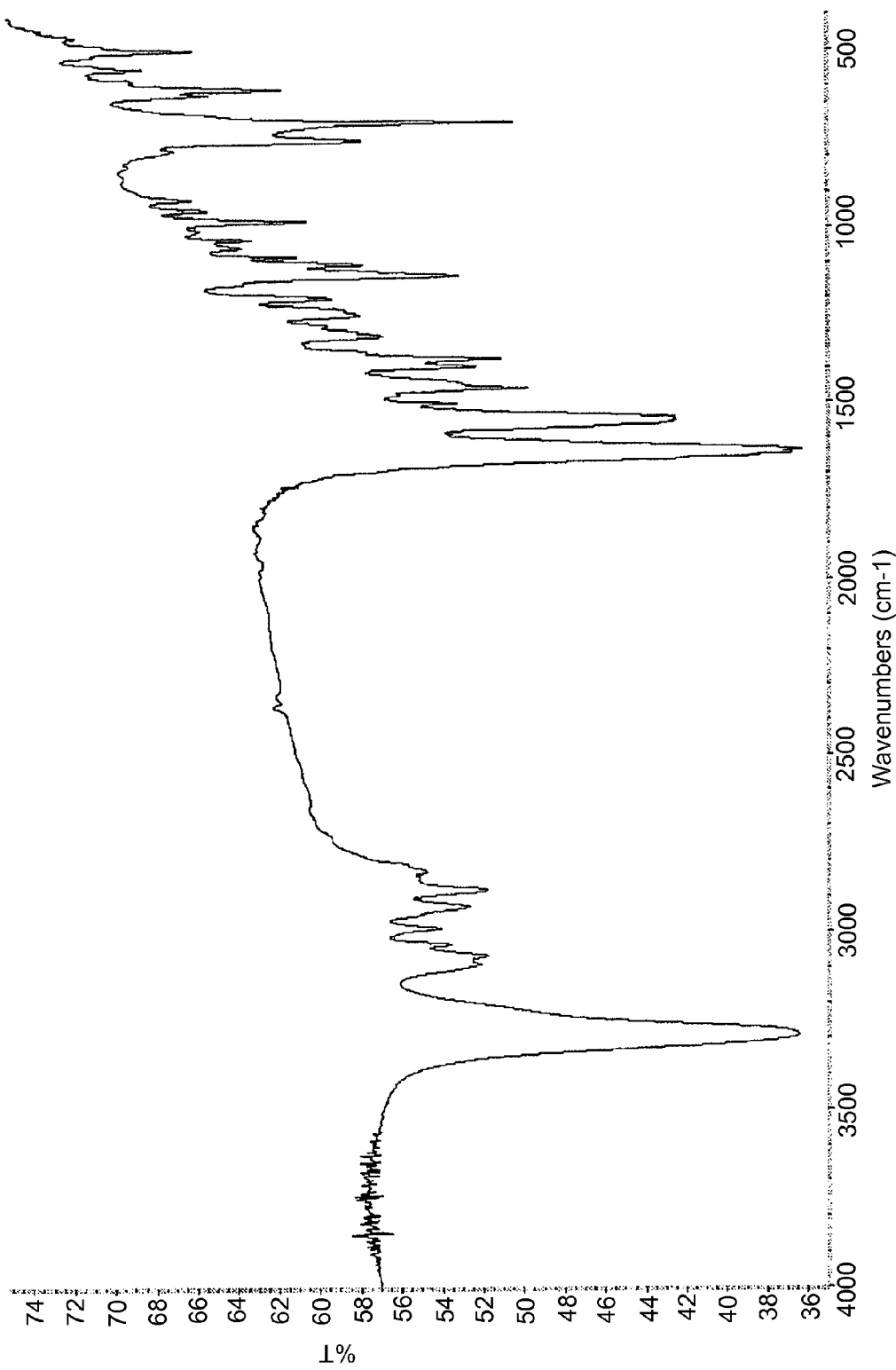
FIG. 5 depicts the Infrared (IR) spectrum of lacosamide crystalline Form II.

Lacosamide crystalline Form II can also be characterized by an IR spectrum comprising characteristic absorption bands at 3290, 3064, 2988, 2928, 2883, 1633, 1548, 1455, 1393, 1371, 1307, 1245, 1198, 1134, 1102, 979, 749, 698, 604, and 494 cm$^{-1}$. FIG. 5 depicts the IR spectrum of lacosamide crystalline Form II.

Lacosamide crystalline Form II can be prepared by crystallizing lacosamide in a suitable solvent at room temperature or reflux temperature of the solvent. Suitable solvents include but are not limited to 2-propanol, 2-methyl-1-propanol, tetrahydrofuran, 2-methyl tetrahydrofuran, ethylal and isopropyl acetate.

Lacosamide crystalline Form II can also be prepared by dissolving lacosamide in a suitable solvent at room temperature or reflux temperature of the solvent, and adding heptane or methyl tert-butyl ether (MTBE) as an antisolvent, thereby precipitating lacosamide crystalline Form II from solution. Suitable solvents include but are not limited to methanol, ethanol, 2-propanol, tetrahydrofuran, acetone, toluene, 1,4-dioxane, chloroform, and dichloromethane.

Figure 6:
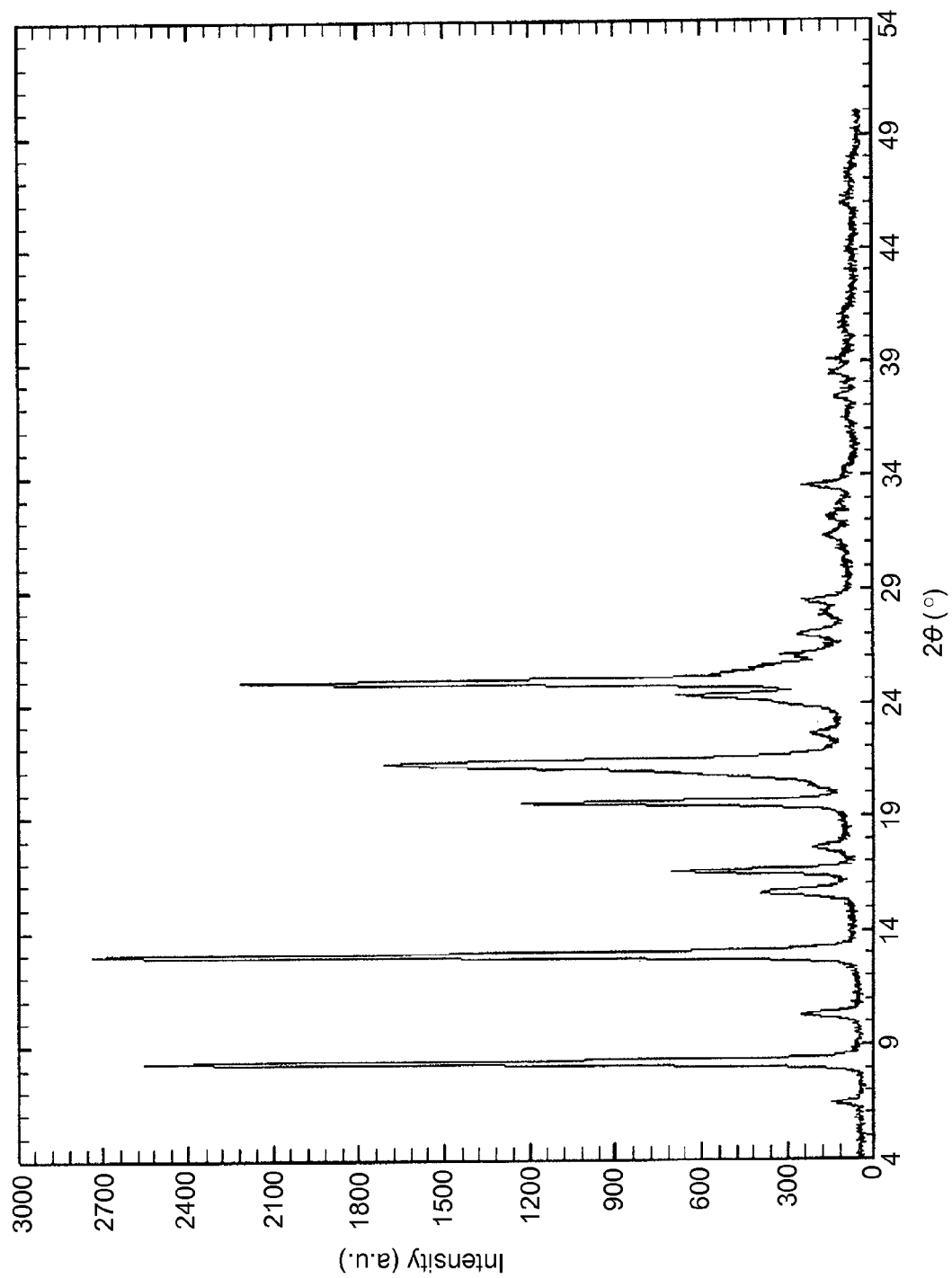
FIG. 6 depicts the X-ray powder diffractogram (XRD) of lacosamide crystalline Form III.

Lacosamide crystalline Form III can be characterized by an XRD pattern comprising peaks (2θ) at 6.5, 8.3, 10.3, 12.9, 15.6, 16.5, 17.5, 19.5, 21.2, 22.5, 24.2, 24.9, 27.0, and 28.5 degrees (±0.2 degrees). FIG. 6 illustrates the XRD of lacosamide crystalline Form III.

Figure 7:
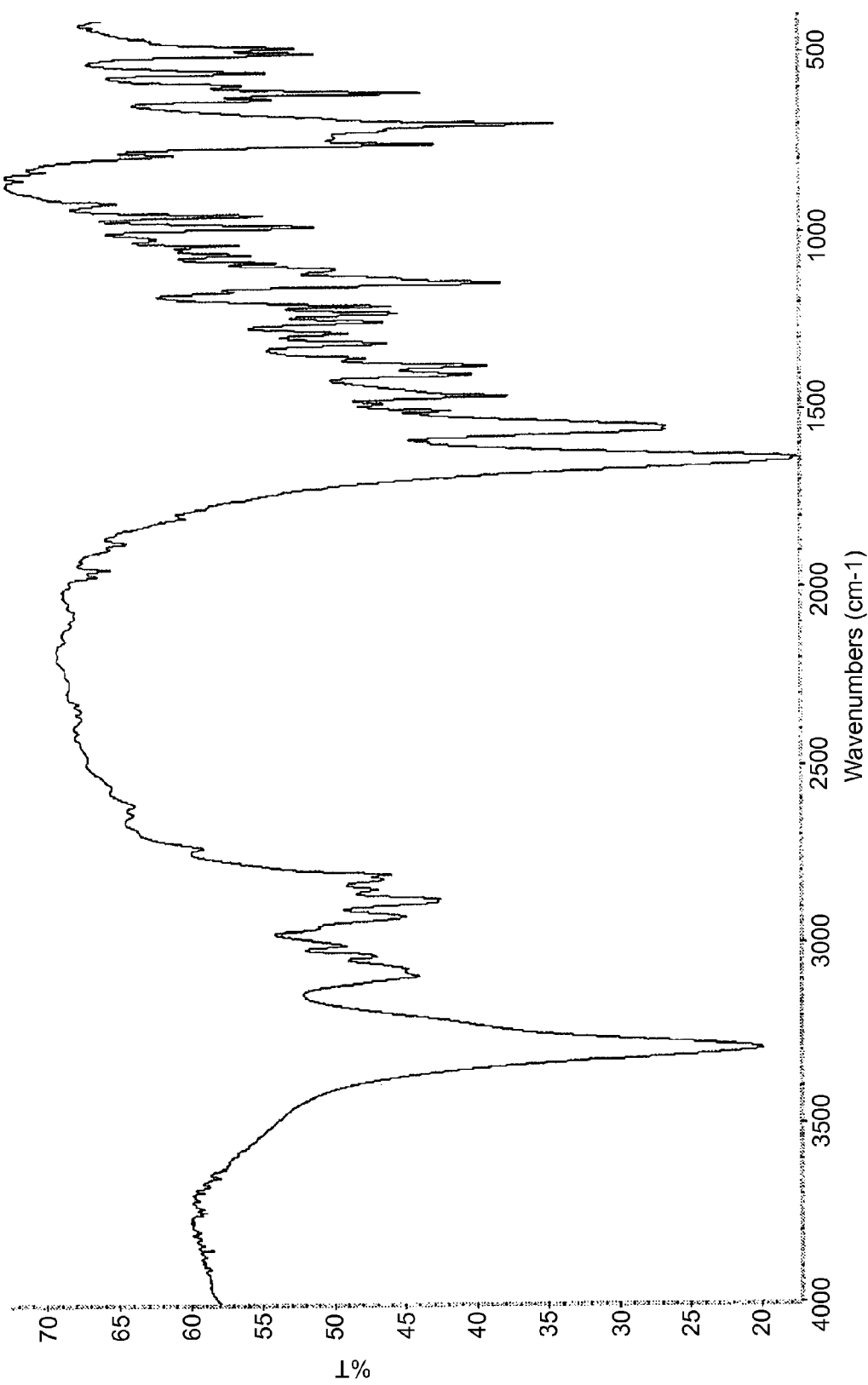
FIG. 7 depicts the Infrared (IR) spectrum of lacosamide crystalline Form III.

Lacosamide crystalline Form III can also be characterized by an IR spectrum comprising characteristic absorption bands at 3291, 3087, 3004, 2924, 2876, 2806, 1635, 1548, 1455, 1395, 1370, 1306, 1276, 1245, 1221, 1202, 1138, 977, 945, 748, 695, 605, 546, 495, and 480 cm$^{-1}$. FIG. 7 depicts the IR spectrum of lacosamide crystalline Form III.

Figure 8:
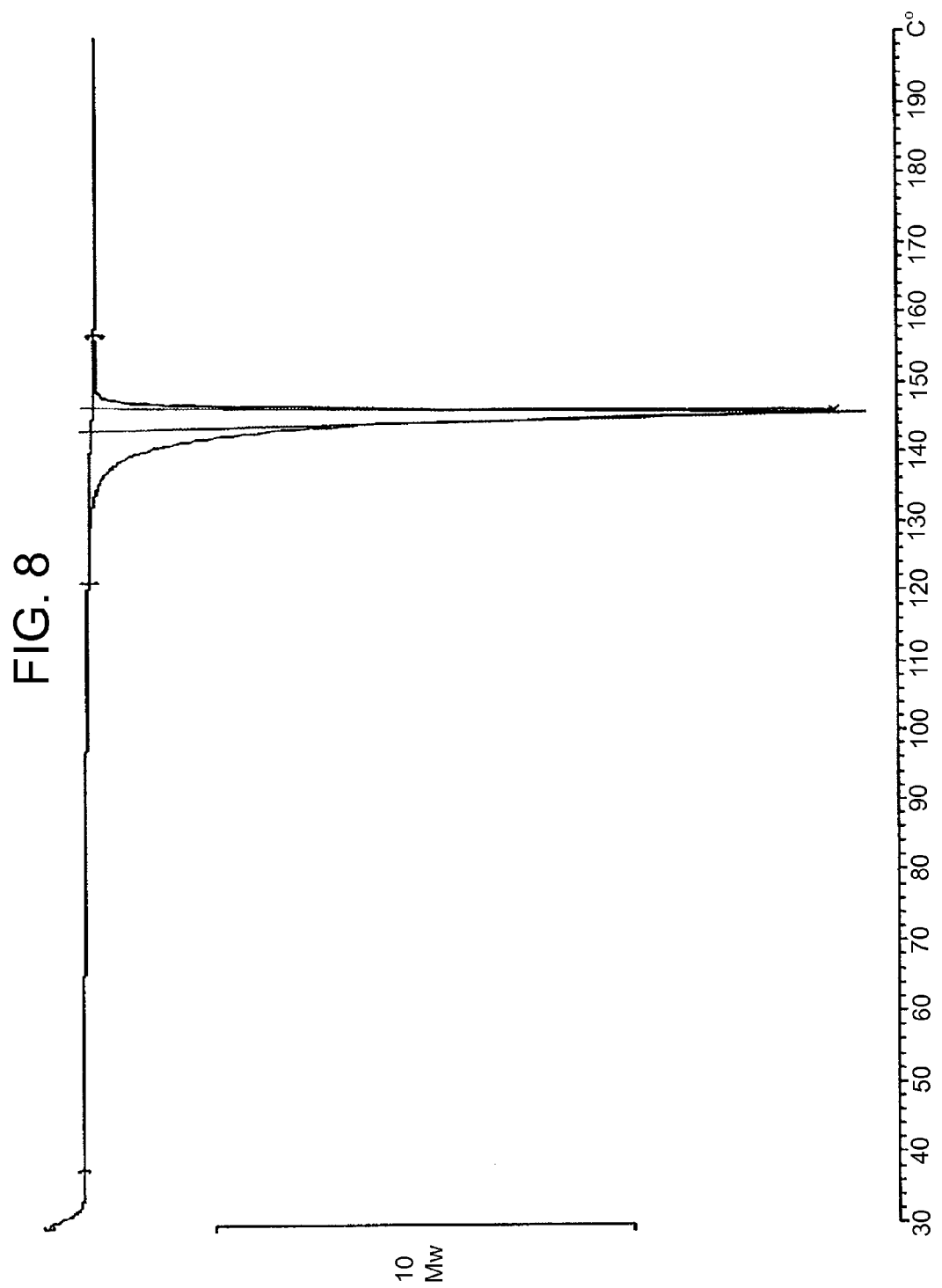
FIG. 8 depicts the DSC of lacosamide crystalline Form III.

Lacosamide crystalline Form III can also be characterized by a melting point of about 143.4° C. (onset temperature) and about 145.0° C. (peak temperature) as measured by DSC. FIG. 8 depicts the DSC plot of lacosamide crystalline Form III.

Lacosamide crystalline Form III corresponds to an anhydrous, non-solvated crystalline Form, and no weight loss is therefore observed by thermogravimetric analysis below the melting point.

Lacosamide crystalline Form III can be prepared by crystallizing lacosamide in a suitable solvent at room temperature or reflux temperature of the solvent. Suitable solvents include but are not limited to ethyl acetate, propyl acetate, methyl ethyl ketone, ethanol, water and mixtures thereof (such as ethanol-water 50:50).

Lacosamide crystalline Form III can also be prepared by dissolving lacosamide in acetonitrile to form an acetonitrile solution and adding heptane to the actonitrile solution, thereby precipitating lacosamide crystalline Form III from solution. Applicants have found that heptane acts as an antisolvent when added to the acetonitrile solution of lacosamide.

Figure 9:
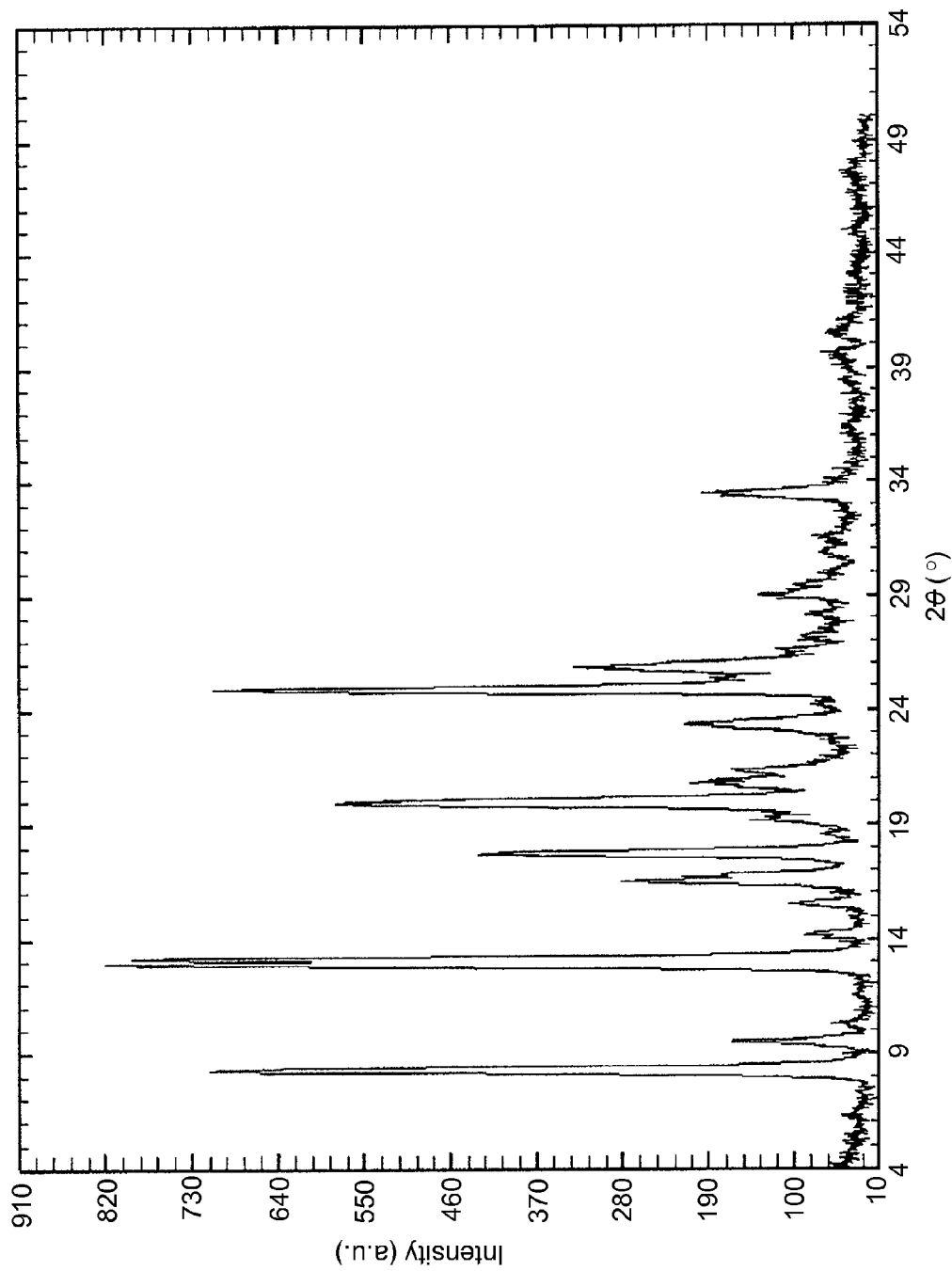
FIG. 9 depicts the X-ray powder diffractogram (XRD) of lacosamide crystalline Form IV.

Lacosamide crystalline Form IV is characterized as a solvate from dichloromethane. Form IV has an XRD pattern comprising peaks (2θ) at 9.5, 14.3, 18.6, 20.0, 23.3 and 25.8 degrees (±0.2 degrees). Form IV can also be more fully described by the additional peaks (2θ) at 8.3, 13.2, 16.5, 17.8, 20.8, 21.3, 24.9, 27.2, 28.2, and 33.5 degrees (±0.2 degrees). FIG. 9 depicts the XRD of lacosamide crystalline Form IV.

Figure 10:
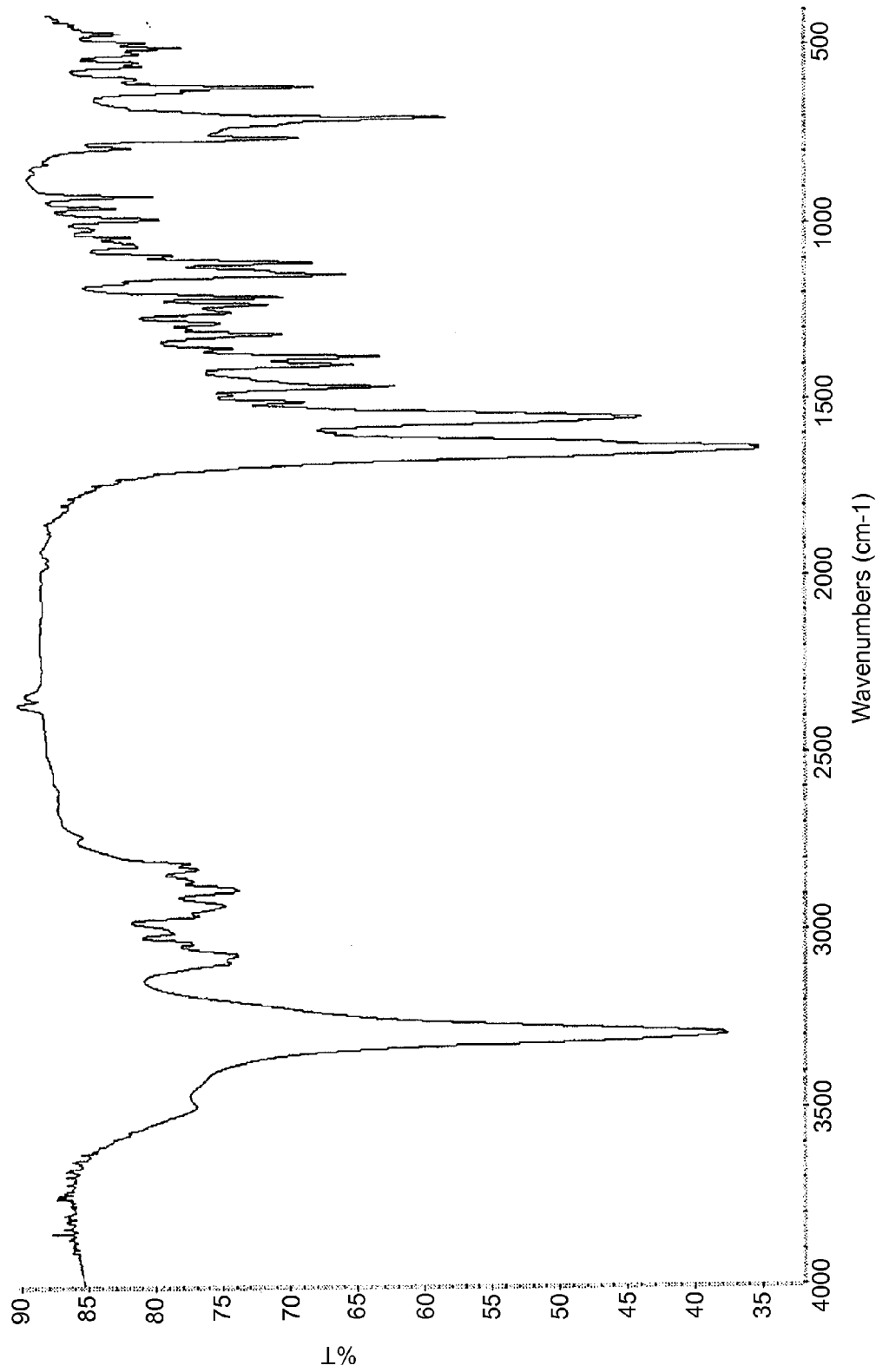
FIG. 10 depicts the Infrared (IR) spectrum of lacosamide crystalline Form IV.

Lacosamide crystalline Form IV can also be characterized by an IR spectrum comprising characteristic absorption bands at 3503, 3291, 3063, 2956, 1640, 1548, 1455, 1394, 1371, 1308, 1275, 1222, 1200, 1138, 1103, 1053, 977, 946, 913, 750, 696, 605, 511, and 455 cm$^{-1}$. FIG. 10 depicts the IR spectrum of lacosamide crystalline Form IV.

Figure 11:
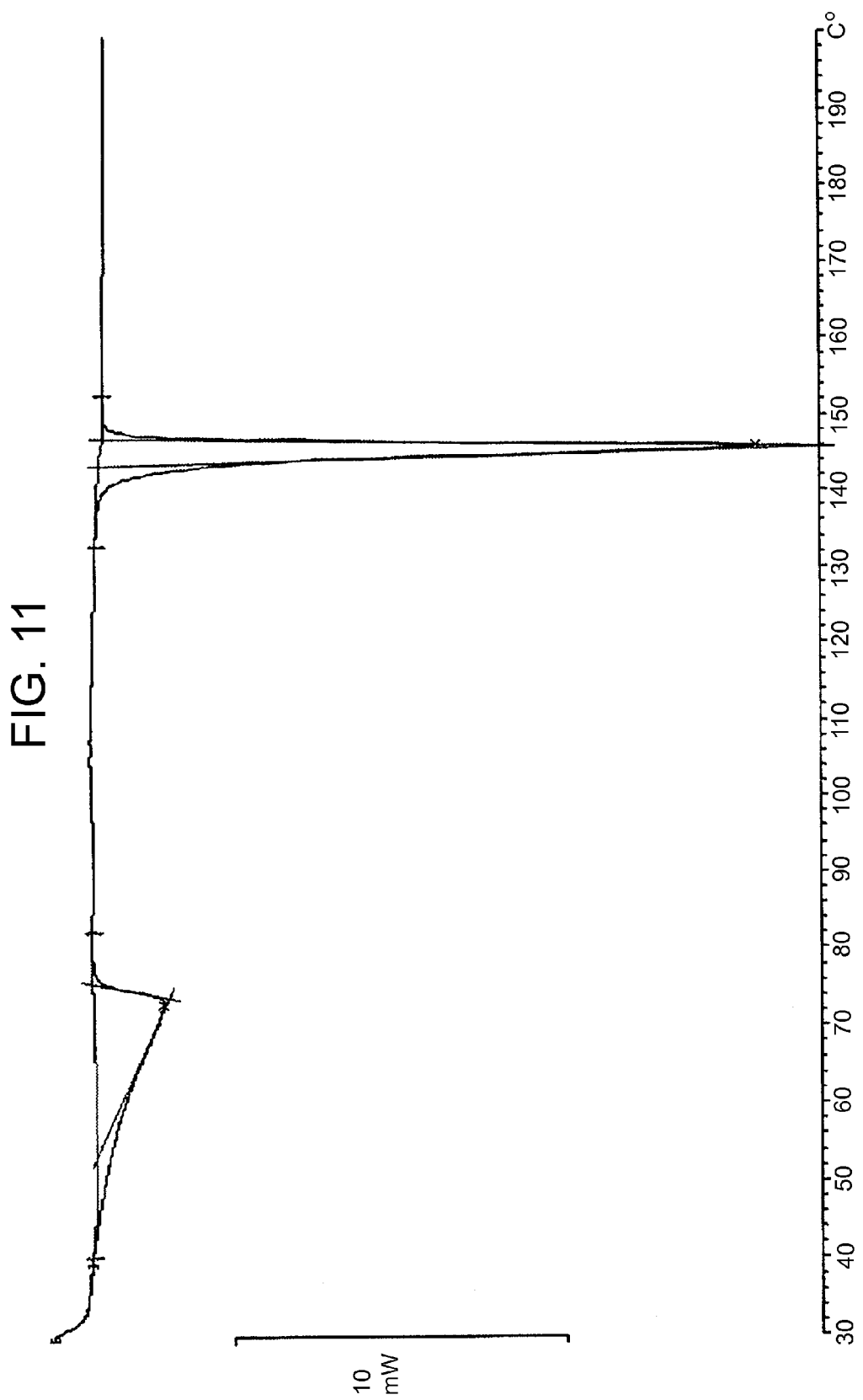
FIG. 11 depicts the DSC of lacosamide crystalline Form IV.

Lacosamide crystalline form IV can also be characterized by a phase transition at about 53.3° C. (onset temperature) and about 73.1° C. (peak temperature) and a melting point of about 143.6° C. (onset temperature) and about 144.9° C. (peak temperature) as measured by DSC. FIG. 11 depicts the DSC plot of lacosamide crystalline Form IV.

Lacosamide crystalline Form IV corresponds to a dichloromethane solvate. A weight loss between about 24.9° C. and about 93.3° C. can be observed by thermogravimetric analysis, due to dichloromethane desolvatation.

Lacosamide crystalline Form IV can be prepared by dissolving lacosamide in dichloromethane and adding heptane as antisolvent, thereby precipitating lacosamide crystalline Form IV from solution.

Lacosamide crystalline Form T can be characterized by an XRD pattern comprising peaks (2θ) at 8.2, 12.9, 16.5, 19.5 and 24.8 degrees (±0.2 degrees).

Specifically, the present invention now provides lacosamide crystalline Form III substantially as herein described and processes of preparing the same.

The provision of Form III in accordance with the present invention can be particularly advantageous in that Form III can exhibit desirable polymorphic stability on storage at ambient conditions for extended periods of storage time, for example on storage at ambient conditions and air atmosphere for at least 250 days, more typically at least 290 days, lacosamide Form III is substantially stable in that substantially no polymorphic interconversion is observed. This desirable stability as associated with Form III can be further illustrated by reference to Examples 61 and 62 herein.

Furthermore, the provision of Form III in accordance with the present invention can be particularly advantageous in that Form III can desirably be crystallized as a conglomerate of the (R)- and (S)-enantiomers of lacosamide substantially as hereinafter described in greater detail. In this way, lacosamide crystalline Form III can offer advantages associated with conglomerate formation, for example efficient and cost effective preparation of enantiomerically enriched lacosamide, again substantially as hereinafter described in greater detail.

The present invention preferably further comprises a polymorphous mixture of crystalline polymorphs of lacosamide substantially as hereinbefore described.

As used herein, "polymorphous mixture", refers to a mixture of polymorphic forms.

Specifically, there is provided a polymorphous mixture comprising lacosamide crystalline Form III as described herein in combination with at least one additional lacosamide crystalline polymorph (e.g., lacosamide crystalline Forms I, II, IV and T). Typically Form III can be present in an amount of about 20 to 80% by weight with the balance % being one or more of Forms I, II, IV and T. In particular, there is provided a polymorphous mixture comprising lacosamide crystalline Forms III and I as described herein.

The amount of lacosamide polymorphs in polymorphous mixtures according to the present invention is expressed herein as a weight ratio of polymorphs as above. Lacosamide may thus be selectively crystallized as a mixture of polymorphs in such a way that the weight ratio between the polymorphs is substantially consistent and within the above defined percent range.

Applicants have also surprisingly discovered that lacosamide can exist in amorphous Form as characterized herein, and furthermore in substantially amorphous Form whereby there is present amorphous lacosamide in admixture with lacosamide crystalline Form III as described herein and optionally also lacosamide crystalline Form I and/or Form II and/or Form IV and/or Form T as described herein. "Substantially amorphous" as referred to herein can denote an amorphous Form of lacosamide which contains less than about 40% by weight of crystalline lacosamide as referred to above, or more preferably less than about 30% by weight of crystalline lacosamide as referred to above, such as typically less than about 20%, less than about 10% and even more typically less than about 5% by weight of crystalline lacosamide as described herein.

Figure 12:
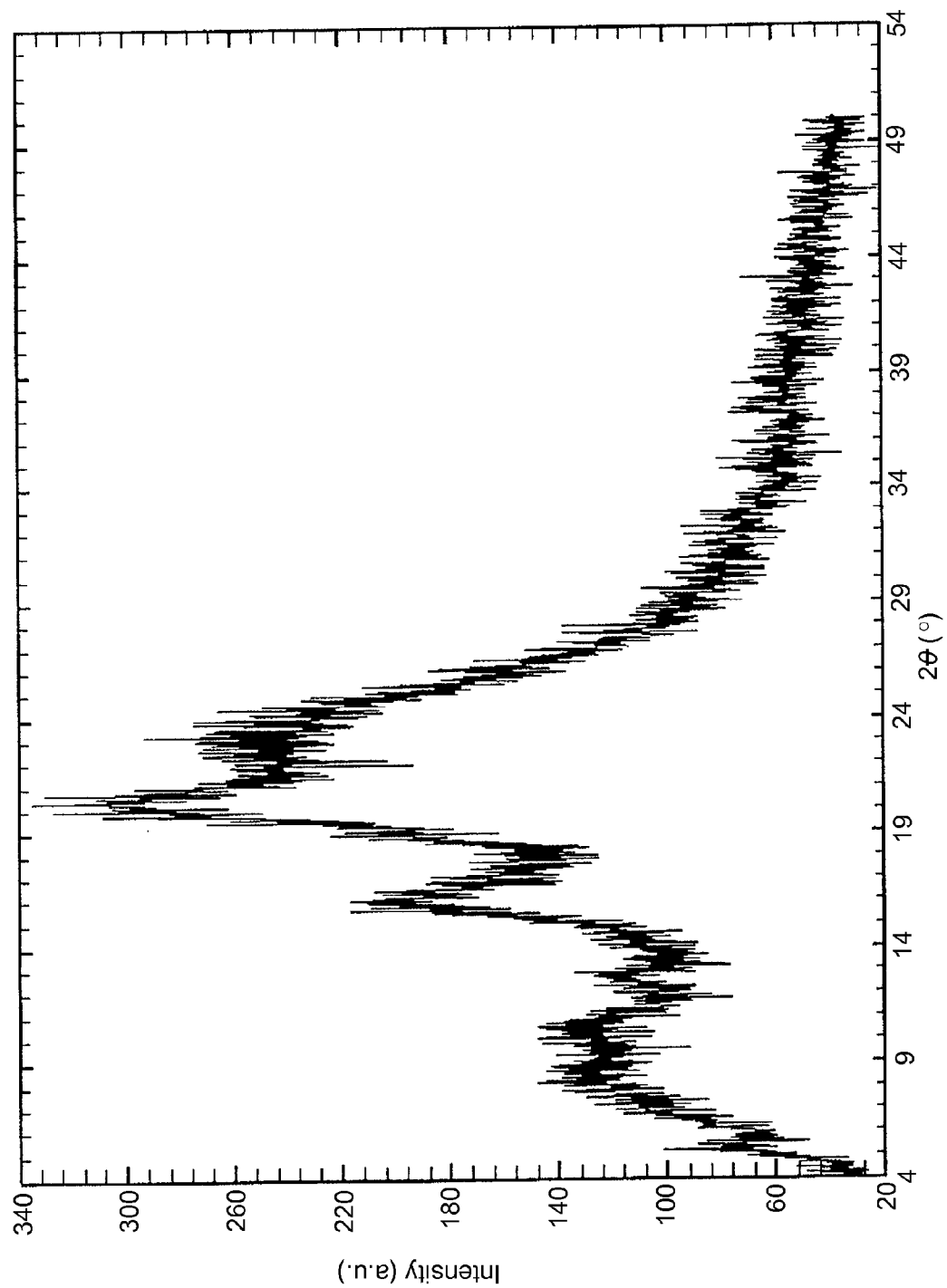
FIG. 12 depicts the X-ray powder diffractogram (XRD) of amorphous lacosamide.

Amorphous lacosamide can be characterized by means of XRD and an XRD pattern therefor is depicted in FIG. 12. Amorphous lacosamide as provided by the present invention can also be provided in admixture with any of lacosamide crystalline Forms I, II, III, IV and T substantially as hereinbefore described.

Amorphous lacosamide can typically be prepared by evaporating a water solution of lacosamide. There is further provided by the present invention amorphous lacosamide obtained, or obtainable, by evaporating a water solution of lacosamide. Suitably the lacosamide used for preparing amorphous Form lacosamide can be lacosamide obtained by any suitable method known in the art.

Figure 13:
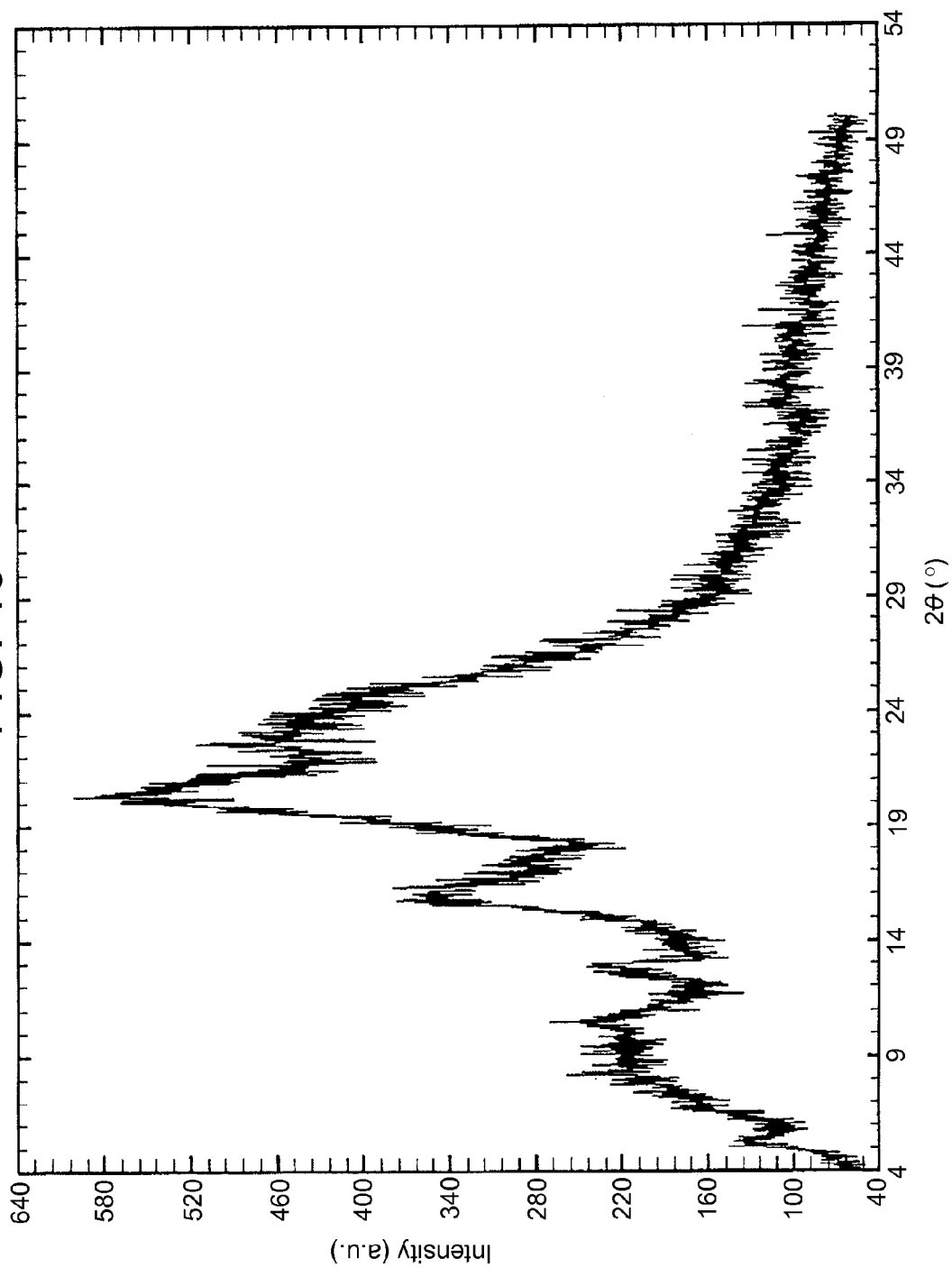
FIG. 13 depicts the X-ray powder diffractogram (XRD) of amorphous lacosamide after stability analysis.

Amorphous lacosamide as provided in accordance with the present invention is also advantageous in that amorphous lacosamide as described herein can exhibit desirable stability on storage at ambient conditions for extended periods of storage time, for example on storage at ambient conditions and air atmosphere for at least 250 days, more typically at least 300 days, amorphous lacosamide according to the present invention is substantially stable. This can be further illustrated by a comparison of FIGS. 12 and 13 herein and the retention of amorphous Form as illustrated by FIG. 13 further to storage as described in Example 63.

The XRDs and associated characterizing data of the lacosamide polymorphs as described herein were obtained using a RX SIEMENS D5000 diffractometer with a vertical goniometer, a copper anodic tube, and radiation $CuK_\alpha$, $\lambda=1.54056$ Å. The IR spectra and associated characterizing data of the lacosamide polymorphs as described herein were obtained on a Thermo Nicolet Nexus spectrometer, and the polymorphs were characterized in potassium bromide pellets. The DSCs and associated characterizing data of the lacosamide polymorphs as described herein were obtained using a Mettler Toledo DSC 823$^e$ (with Mettler Toledo STAR$^e$ SW 9.20 software). The samples were placed in open pan types under nitrogen purge and sample weights were between 2 to 3 mg. DSC experiments were run from 30 to 200° C. at a heating rate of 10° C./minute.

It has also now been found in accordance with the present invention that lacosamide can exist as a conglomerate. The frequency of occurrence of conglomerates is rare and only expected in approximately between 5 and 10% of compounds, see J. Jacques, A. Collet and S. H. Wilden, Enantiomers, Racemates and Resolutions, Krieger Publishing Company, 1991, p 53 and K. Saigo et al, *J. Am. Chem. Soc.,* 118, 3441-3449 (1996). A conglomerate is a mechanical mixture of enantiomerically pure crystals of one enantiomer and its opposite. Molecules in the crystal structure have a greater affinity for the same enantiomer than for the opposite enantiomer. Therefore, it has been found that lacosamide can be enantiomerically purified by direct, preferential crystallization. The advantage of increasing the enantiomeric excess by direct crystallization is evident given that conglomerate resolution may be operated as a continuous process which is often extremely efficient for multi-ton manufacture, see J. Crosby, *Tetrahedron,* 47, 4789 (1991).

Identification of a conglomerate is achieved by analysis of the physical characteristics of the solid Form. Examples of such techniques include, but are not limited to, infrared spectroscopy, X-ray powder diffraction and differential scanning calorimetry. In such techniques, a racemic sample is usually compared to a sample that has been enantiomerically enriched. By infrared spectroscopy and X-ray powder diffraction analysis, conglomerate samples will be identical in all enantiomeric compositions, see J. Jacques, A. Collet and S. H. Wilden, Enantiomers, Racemates and Resolutions, Krieger Publishing Company, 1991, p 53. On the other hand, the melting point (as measured for example by differential scanning calorimetry) of the racemic conglomerate is always lower than that of the pure enantiomers. The lowest melting point corresponds to the racemic mixture, and the melting point is increased by increasing the enantiomeric excess of the enantiomeric mixture, showing a typical eutectic behaviour.

According to the present invention, therefore, there is further provided a mixture of lacosamide (R)- and (S)-enantiomers crystallized in a conglomerate Form. Typically in such a mixture of lacosamide (R)- and (S)-enantiomers crystallized in a conglomerate Form in accordance with the present invention, the (R)-enantiomer of lacosamide is present in an amount of at least about 50% by weight, more preferably at least about 80% by weight (suitably at least 60% enantiomeric excess); still more preferably at least about 90% by weight (suitably at least 80% enantiomeric excess); particularly more preferably at least about 95% by weight (suitably at least 90% enantiomeric excess); yet more preferably at least about 98% by weight (suitably at least 96% enantiomeric excess); and even more preferably at least about 99% by weight (suitably at least 98% enantiomeric excess). A lacosamide conglomerate as thus provided by the present invention also preferably comprises one or more polymorphs of lacosamide and/or mixtures thereof substantially as hereinbefore described and as such provides advantages for such polymorphs of lacosamide and/or mixtures thereof, that can be associated with a conglomerate. It is also therefore further preferred that the present invention provides a mixture of lacosamide (R)- and (S)-enantiomers crystallized in a conglomerate Form substantially as described above, wherein the lacosamide is present in the conglomerate as crystalline Form III substantially as hereinbefore described, and/or crystalline Form I substantially as hereinbefore described, and/or crystalline Form II substantially as hereinbefore described.

There is also provided a process of separating the (R)- and (S)-enantiomers of lacosamide by carrying out at least one direct crystallization of the mixture of lacosamide enantiomers crystallized in a conglomerate Form as provided by the present invention. Again, lacosamide preferably comprises one or more polymorphs of lacosamide and/or mixtures thereof substantially as hereinbefore described. In particular, it is preferred that the present invention provides a process of separating the (R)- and (S)-enantiomers of lacosamide by carrying out at least one direct crystallization of the mixture of lacosamide enantiomers crystallized in a conglomerate Form wherein the lacosamide is present as crystalline Form III substantially as hereinbefore described, or crystalline Form I substantially as hereinbefore described, or crystalline Form II substantially as hereinbefore described, or crystalline Form III in admixture with crystalline Form I substantially as hereinbefore described and/or crystalline Form II substantially as hereinbefore described.

Preferably the present invention further provides a process for the preparation of enantiomerically enriched lacosamide, which process comprises providing a supersaturated solution of lacosamide, seeding the supersaturated solution of lacosamide with enantiomerically enriched lacosamide and recovering enantiomerically enriched lacosamide as a conglomerate that directly crystallizes out of the solution. Again, lacosamide is typically present as one or more polymorphs of lacosamide and/or mixtures thereof substantially as hereinbefore described. In particular, it is preferred that the present invention provides a process for the preparation of enantiomerically enriched lacosamide, which process comprises providing a supersaturated solution of lacosamide, seeding the supersaturated solution of lacosamide with enantiomerically enriched lacosamide and recovering enantiomerically enriched lacosamide as a conglomerate that directly crystallizes out of the solution, wherein the lacosamide is present as crystalline Form III substantially as hereinbefore described, or crystalline Form I substantially as hereinbefore described, or crystalline Form II substantially as hereinbefore described, or crystalline Form III in admixture with crystalline Form I substantially as hereinbefore described and/or crystalline Form II substantially as hereinbefore described.

Preferably the present invention further provides a process for the preparation of enantiomerically enriched lacosamide, which process comprises providing a supersaturated solution of lacosamide comprising an epimerization agent, such as a basic catalyst, that affords interconversion of the enantiomers by epimerization of the chiral centre, seeding the supersaturated solution of lacosamide with enantiomerically enriched lacosamide and recovering enantiomerically enriched lacosamide as a conglomerate that directly crystallizes out of the solution. Again, lacosamide is typically present as one or more polymorphs of lacosamide and/or mixtures thereof substantially as hereinbefore described. In particular, it is preferred that the present invention provides a process for the preparation of enantiomerically enriched lacosamide, which process comprises providing a supersaturated solution of lacosamide comprising an epimerization agent, such as a basic catalyst, that affords interconversion of the enantiomers by epimerization of the chiral centre, seeding the supersaturated solution of lacosamide with enantiomerically enriched lacosamide and recovering enantiomerically enriched lacosamide as a conglomerate that directly crystallizes out of the solution, wherein the lacosamide is present as crystalline Form III substantially as hereinbefore described, or crystalline Form I substantially as hereinbefore described, or crystalline Form II substantially as hereinbefore described, or crystalline Form III in admixture with crystalline Form I substantially as hereinbefore described and/or crystalline Form II substantially as hereinbefore described.

Preferably, the present invention further provides a process for increasing the enantiomeric excess of an enantiomerically enriched lacosamide, which process comprises carrying out at least one direct crystallization of a solution of the enantiomerically enriched lacosamide and recovering enantiomerically enriched lacosamide as a conglomerate that directly crystallizes out of the solution. Again, lacosamide is typically present as one or more polymorphs of lacosamide and/or mixtures thereof substantially as hereinbefore described. In particular, it is preferred that the present invention provides a process for increasing the enantiomeric excess of an enantiomerically enriched lacosamide, which process comprises carrying out at least one direct crystallization of a solution of the enantiomerically enriched lacosamide and recovering enantiomerically enriched lacosamide as a conglomerate that directly crystallizes out of the solution, wherein the lacosamide is present as crystalline Form III substantially as hereinbefore described, or crystalline Form I substantially as hereinbefore described, or crystalline Form II substantially as hereinbefore described, or crystalline Form III in admixture with crystalline Form I substantially as hereinbefore described and/or crystalline Form II substantially as hereinbefore described.

"Enantiomerically enriched lacosamide" that can be employed in a seeding step of a process as described herein, can typically be prepared by a process according to the present invention, or by classical resolution of racemic lacosamide, or by asymmetric synthesis, or by enzymatic resolution processes.

Typically, a conglomerate of lacosamide as provided by the present invention and/or enantiomerically enriched lacosamide is crystallized from a suitable solvent, preferably ethyl acetate.

It is preferred that enantiomerically enriched lacosamide as prepared according to the present invention comprises lacosamide enriched with the (R)-enantiomer. "Enantiomerically enriched" as referred to herein typically denotes at least about 60% enantiomeric excess or more typically at least about 80% enantiomeric excess, and more preferably at least about 90% or about 96% or about 98% enantiomeric excess, as measured by % area by HPLC. Typically, the (S)-enantiomer is present in an amount of less than about 20%, or preferably less than about 10%, or about 5%, or about 2%, or about 1%, as measured by % area by HPLC.

There is also provided by the present invention a mixture of lacosamide enantiomers crystallized in a conglomerate Form, or enantiomerically enriched lacosamide obtained from the mixture, obtained by crystallization from a solvent preferred for providing lacosamide either as crystalline Form III and/or Form II and/or Form I substantially as hereinbefore described. Preferably the solvent is selected from the group consisting of water, methanol, ethanol, 2-butanol, 1-pentanol, 2-ethoxy ethanol, acetone, methyl ethyl ketone, methyl isobutyl ketone, cyclopentanone, chloroform, acetonitrile, methyl tert-butyl ether, tetrahydrofuran, 1,3-dioxolane, 1,4-dioxane, heptane, methyl cyclohexane, ethylal, ethyl acetate, propyl acetate, n-butyl acetate, isobutyl acetate, 2-propanol, 2-methyl-1-propanol, 2-methyl tetrahydrofuran, toluene, dichloromethane, and/or mixtures thereof. More preferably, the solvent is ethyl acetate.

Lacosamide as provided by the present invention can be used in pharmaceutical compositions comprising lacosamide and one or more pharmaceutically acceptable excipients therefor.

Accordingly the present invention further provides a pharmaceutical composition comprising lacosamide substantially as hereinbefore described and at least one pharmaceutically acceptable excipient.

In another embodiment, the invention encompasses a process for preparing a pharmaceutical composition comprising lacosamide substantially as hereinbefore described and at least one pharmaceutically acceptable excipient.

A pharmaceutical composition according to the present invention can be in a solid or a non-solid form and typically comprises tablets, powders, capsules, suppositories, sachets, troches and lozenges. The treatment effective amount or proper dosage to be used can be determined by one of ordinary skill in the art, which can depend on the method of administration, the bioavailability, the age, sex, symptoms and health condition of the patient, and the severity of the disease to be treated, etc.

In another embodiment, the invention encompasses the use of lacosamide substantially as hereinbefore described for use as an anticonvulsant and/or for relieving pain.

In yet another embodiment, the present invention encompasses a method of treating central nervous system disorders, in particular epilepsy, and alleviating pain comprising administering to a subject in need thereof a pharmaceutical composition comprising lacosamide substantially as hereinbefore described and at least one pharmaceutically acceptable excipient. In one embodiment, the method include administering to a subject suffering from a central nervous system disorder an anti-convulsant effective amount of any of the Forms of lacosamide substantially as hereinbefore described. For example, the disorder may be epilepsy. In another embodiment the methods include administering to a subject suffering from neuropathic pain a pain-reducing effective amount of lacosamide substantially as hereinbefore described. For example, the neuropathic pain can be diabetic neuropathic pain. In other embodiments, the methods include administering to a subject suffering from migraine headache a headache-reducing effective amount of lacosamide substantially as hereinbefore described.

The following examples further illustrate the invention but, of course, should not be construed as in any way limiting its scope.

EXAMPLES

General Experimental Conditions

X-ray Powder Diffraction (XRD)
The XRDs were obtained using a RX SIEMENS D5000 diffractometer with a vertical goniometer, a copper anodic tube, and radiation $CuK_\alpha$, $\lambda=1.54056$ Å.
Infrared Spectra (IR)
Fourier transform IR spectra were acquired on a Thermo Nicolet Nexus spectrometer, and polymorphs were characterized in potassium bromide pellets.
Differential Scanning Calorimetry (DSC)
The Differential Scanning calorimeter used was a Mettler Toledo DSC 823$^e$ with Mettler Toledo STAR$^e$ SW 9.20 software. Samples were placed in open (hermetically sealed aluminium with a vent hole) pan types under nitrogen purge. Sample weights were between 2 to 3 mg. DSC experiments were run from 30 to 200° C. at a heating rate of 10° C./minute.
High Performance Liquid Chromatography Method (HPLC):
The chromatographic separation was carried out in a Lux Cellulose 2, 5 µm, 250×4.6 mm I.D column; 40° C. The mobile phase was isopropanol/ethanol/n-hexane (28:10:62). The chromatograph was equipped with a 215 nm detector and the flow rate was 0.8 ml per minute. 10 µl of the test samples prepared by dissolving the appropriate amount of sample to obtain 2 mg/ml of a solution in ethanol were injected.
Lacosamide Starting Material:
Lacosamide as used as a starting material for Examples 1 to 50 was commercially available lacosamide that is essentially enantiomerically pure having less than 0.022% of the (S)-enantiomer of lacosamide.

Crude Lacosamide as used as a starting material for Examples 51 to 60 was prepared so as follows.

Intermediate 1: Preparation of (2R)-2-[(tert-butoxycarbonyl)amino]-3-hydroxypropanoic acid To a cold solution (5° C.) of 74.4 g (1.86 mol) of sodium hydroxide in 1800 mL of water was added 95.1 g (0.90 mol) of D-serine. Then, a solution of 274.5 g (1.26 mol) of di-tert-butyldicarbonate ($BOC_2O$) in 840 mL of 1,4-dioxane was added dropwise maintaining the temperature below 10° C. The reaction was stirred during 1 hour at 10° C. and for 2 hours at room temperature. The pH was adjusted to 10 with 50% sodium hydroxide (19.0 mL) and the reaction mixture was stirred at room temperature for 15 hours. Half of the reaction volume was evaporated under vacuum and after cooling the residue to 5° C. the pH was adjusted to 2-3 using 1N $NaHSO_4$. The mixture was extracted with ethyl acetate (5×1000 mL) and the combined organic phase was dried over sodium sulphate and concentrated under vacuum. The resulting oil was dissolved in methyl tert-butyl ether (200 mL), petroleum oil (800 mL) was added and the mixture was stirred for 1 hour. The solid was collected by filtration and dried yielding 158.3 g of the title compound as a white solid (Yield 85%).

Intermediate 2: Preparation of (2R)-2-[(tert-butoxycarbonyl)amino]-3-(tetrahydro-2H-pyran-2-yloxy) propanoic acid To a stirred solution of 2.32 g (0.012 mol) of p-toluensulfonic acid and 0.95 g (0.012 mol) of pyridine in 250 mL of dichloromethane, 25.0 g (0.12 mol) of Intermediate 1 was added. Then, 24.22 g (0.29 mol) of dihydropyran was added dropwise and the resulting mixture was stirred overnight at room temperature. The solvent was removed under vacuum and the residue was redissolved in ethyl acetate (350 mL). The organic phase was washed with water (2×250 mL) and dried over sodium sulphate. The solvent was evaporated under vacuum and 49.00 g of a pale yellow oil was obtained. The oil was not purified and used directly in the following step.

Intermediate 3: Preparation of tert-butyl {(2R)-2-(benzylamino)-2-oxo-1-[(tetrahydro-2H-pyran-2-yloxy)methyl]ethyl}carbamate To a cold solution (5° C.) of 10.00 g of Intermediate 2 in 150 mL of dichloromethane was added 5.89 g (0.036 mol) of 1,1'-carbonyldiimidazole. The mixture was allowed to warm to room temperature and stirred for 1.5 hours. Then, it was cooled to 5° C. and 4.37 g (0.041 mol) of benzylamine was added dropwise and the reaction was stirred at room temperature overnight. The organic phase was washed with 1 M HCl (2×80 mL), sodium bicarbonate solution (2×80 mL), water (80 mL), brine (80 mL) and dried over sodium sulfate. The solvent was evaporated under vacuum yielding 14.36 g as an oil. The oil was not purified and used directly in the following step.

Intermediate 4: Preparation of tert-butyl [(2R)-1-(benzylamino)-3-hydroxy-1-oxopropan-2-yl]carbamate A solution of 12.86 g of Intermediate 3 and 0.65 g of p-toluensulfonic acid in 100 mL of ethanol was heated at reflux temperature for 2 hours. The solvent was evaporated under vacuum and to the residue was added ethyl acetate (100 mL) which resulted in the precipitation of a white solid. The solvent was partially distilled and 150 mL of petroleum oil was added and stirred overnight. The solid was collected by filtration and dried yielding 6.5 g of the title compound as a white solid.

Intermediate 5: Preparation of tert-butyl [(2R)-1-(benzylamino)-3-methoxy-1-oxopropan-2-yl]carbamate To a stirred solution of 3.2 g (0.01 mol) of Intermediate 4 in 50 mL of toluene was added 0.61 g of tetrabutylammonium bromide and 5 ml of water. The resulting mixture was cooled to 10° C. and a solution of 2.4 g of sodium hydroxide in 2.5 ml of water was added dropwise maintaining the temperature below 10° C. Then, 5.54 g of dimethylsulfate was added dropwise maintaining the temperature below 10° C. After stirring at 10° C. for 2 hours, water (80 mL) was added and the reaction stirred at room temperature overnight. The layers were separated and the aqueous layer was washed twice with dichloromethane (50 mL). The combined organic phase was washed with sodium bicarbonate solution (2×30 mL) and brine. The solvent was removed under vacuum yielding 3.36 g of a pale red-oil. The oil was not purified and used directly in the following step.

Intermediate 6: Preparation of (2R)-2-amino-N-benzyl-3-methoxypropanamide

To a cold solution (5° C.) of 3.36 g of Intermediate 5, benzylamide in 40 mL of dichloromethane was added 6.02 mL of 36% HCl. The reaction mixture was stirred at room temperature until no starting material was observed by TLC. The organic phase was washed with 1N HCl (2×30 mL) and the combined aqueous phase basified to 10-12 with 25% NaOH. After saturating the aqueous phase with sodium chloride, it was extracted with dichloromethane (3×30 mL). The organic phase was dried and concentrated under vacuum yielding 2.01 g of a pale yellow oil.

Crude Lacosamide Preparation of (2R)-2-(acetylamino)-3-methoxy-N-phenylmethyl)propanamide To a cold solution (−2° C.) of 1.94 g of Intermediate 6, in 40 mL of dichloromethane was added dropwise 2.12 g of acetic anhydride maintaining the temperature below 5° C. The reaction mixture was stirred at room temperature for 3 hours and the organic phase was washed with water (2×20 mL), sodium bicarbonate solution (2×20 mL), brine and dried over sodium sulfate. The solvent was removed under vacuum and a white solid was obtained. The product was dissolved in 20 mL of ethyl acetate at reflux temperature and cooled slowly to 0° C. The solid was collected by filtration and dried yielding 1.6 g of lacosamide as a white solid.

Examples 1-14

Preparation of Lacosamide Crystalline Form I

These examples illustrate a process for preparing lacosamide crystalline Form I.

Lacosamide (150 mg) was dissolved in a solvent at room temperature or reflux temperature of the solvent (see Table 1). The solutions were allowed to cool to room temperature (if necessary) and were filtered or the solvent slowly evaporated at ambient pressure/temperature, or at 40° C. under vacuum. The obtained solids were analyzed by XRD.

The results are listed in Table 1.

TABLE 1

| Example | Solvent | Volume (mL) | Temperature | Drying | XRD |
|---|---|---|---|---|---|
| 1 | chloroform | 0.5 | r.t. | r.t. | Form I |
| 2 | methanol | 1 | r.t. | r.t. | Form I |
| 3 | acetone | 1 | reflux | r.t. | Form I |
| 4 | ethanol | 1 | reflux | r.t. | Form I |
| 5 | methyl tert-butyl ether | 10 | reflux | r.t. | Form I |
| 6 | 2-butanol | 1 | reflux | 40° C. under vacuum | Form I |
| 7 | methyl isobutyl ketone | 1 | reflux | filtered | Form I |
| 8 | methyl cyclohexane | 1 | reflux | filtered | Form I |
| 9 | cyclopentanone | 1 | reflux | filtered | Form I |
| 10 | 2-ethoxy ethanol | 1 | reflux | 40° C. under vacuum | Form I |
| 11 | 1-pentanol | 1 | reflux | 40° C. under vacuum | Form I |
| 12 | isobutyl acetate | 1 | reflux | 40° C. under vacuum | Form I |
| 13 | tetrahydrofuran | 1 | reflux | filtered | Form I |
| 14 | 1,3-dioxolane | 1 | reflux | 40° C. under vacuum | Form I |

Examples 15-17

Preparation of Lacosamide Crystalline Form I

These examples illustrate a further process for preparing lacosamide crystalline Form I.

Lacosamide (150 mg) was suspended in a solvent at room temperature or reflux temperature for 1 h (see Table 2). The solid was filtered and analyzed by XRD.

The results are listed in Table 2.

TABLE 2

| Example | Solvent | Volume (mL) | Temperature | XRD |
|---|---|---|---|---|
| 15 | n-butyl acetate | 10 | r.t. | Form I |
| 16 | heptane | 10 | r.t. | Form I |
| 17 | heptane | 10 | reflux | Form I |

Example 18

Preparation of Lacosamide Crystalline Form I

This example illustrates a further process for preparing lacosamide crystalline Form I.

Lacosamide (150 mg) was suspended in water (1.5 mL) and stirred at room temperature for 2 days. The solid was filtered and analyzed by XRD.

Examples 19-24

Preparation of Lacosamide Crystalline Form I

These examples illustrate a further process for preparing lacosamide crystalline Form I.

Lacosamide (150 mg) was dissolved at room temperature or reflux temperature in the solvent indicated in Table 3. Then heptane or methyl tert-butyl ether (MTBE) was added as an antisolvent in the amount indicated in Table 3, and the mixture was stirred for 30 min. at the same temperature and then cooled to room temperature for 1-2 h. The solid was filtered and analyzed by XRD.

The results are listed in Table 3.

TABLE 3

| Example | Solvent | Anti-solvent | $V_S:V_{AS}$ (mL:mL) | Temperature | XRD |
|---|---|---|---|---|---|
| 19 | acetone | Heptane | 1:2 | reflux | Form I |
| 20 | toluene | | 1.5:2 | reflux | Form I |
| 21 | 1,4-dioxane | | 1:3 | reflux | Form I |
| 22 | chloroform | | 0.5:3 | r.t. | Form I |
| 23 | acetonitrile | MTBE | 1:5 | reflux | Form I |
| 24 | tetrahydrofuran | | 1:5 | reflux | Form I |

Examples 25-27

Preparation of Lacosamide Crystalline Form II

These examples illustrate a process for preparing lacosamide crystalline Form II.

Lacosamide (150 mg) was dissolved at room temperature or reflux temperature in the solvent indicated in Table 4. The solutions were allowed to cool to room temperature, if necessary, and the obtained residue was air dried and analyzed by XRD.

The results are listed in Table 4.

TABLE 4

| Example | Solvent | Volume (mL) | Temperature | XRD |
|---|---|---|---|---|
| 25 | tetrahydrofuran | 5.5 | r.t | Form II |
| 26 | 2-propanol | 1 | reflux | Form II |
| 27 | isopropyl acetate | 1 | reflux | Form II |

Examples 28-30

Preparation of Lacosamide Crystalline Form II

These examples illustrate a further process for preparing lacosamide crystalline Form II.

Lacosamide (150 mg) was dissolved at reflux in the indicated solvents (Table 5). Ethylal is diethoxymethane. The solutions where allowed to cool to room temperature. The residue obtained was filtered or dried at 40° C. under vacuum as indicated in Table 5. The solid was analyzed by XRD.

The results are listed in Table 5.

TABLE 5

| Example | Solvent | Volume (mL) | Temperature | Work-up | XRD |
|---|---|---|---|---|---|
| 28 | 2-methyl 1-propanol | 1 | 100° C. | Dried under vacuum at 40° C. | Form II |
| 29 | 2-methyl tetrahydrofuran | 1 | reflux | Filtered | Form II |
| 30 | ethylal | 10 | reflux | Filtered | Form II |

Examples 31-40

Preparation of Lacosamide Crystalline Form II

These examples illustrate a further process for preparing lacosamide crystalline Form II.

Lacosamide (150 mg) was dissolved in the solvent and at the temperature indicated in Table 6. Then antisolvent was added. The mixture was stirred for 30 minutes at the temperature indicated and then stirred for an additional 1-2 hours at room temperature. The solid was filtered and analyzed by XRD. MTBE is methyl tert-butyl ether.

The results are listed in Table 6.

TABLE 6

| Example | Solvent | Anti-solvent | $V_S:V_{AS}$ (mL:mL) | Temperature | XRD result |
|---|---|---|---|---|---|
| 31 | ethanol | Heptane | 1:5 | reflux | Form II |
| 32 | 2-propanol | | 1:5 | reflux | Form II |
| 33 | tetrahydrofuran | | 1:2 | reflux | Form II |
| 34 | acetone | MTBE | 1:5 | reflux | Form II |
| 35 | methanol | | 1:5 | reflux | Form II |
| 36 | 2-propanol | | 1:5 | reflux | Form II |
| 37 | toluene | | 1.5:2 | reflux | Form II |
| 38 | 1,4-dioxane | | 1:5 | reflux | Form II |
| 39 | chloroform | | 0.5:3 | r.t. | Form II |
| 40 | dichloromethane | | 1.5:5 | r.t. | Form II |

Examples 41-46

Preparation of Lacosamide Crystalline Form IIII

These examples illustrate a process for preparing lacosamide crystalline Form III in accordance with the invention.

Lacosamide (150 mg) was dissolved at room temperature or reflux temperature in the solvents indicated in Table 7. The solution was allowed to cool to room temperature, if necessary, and evaporated at room temperature and pressure. The solid obtained was smoothly ground and analyzed by XRD.

The results are listed in Table 7.

TABLE 7

| Example | Solvent | Volume (mL) | Temperature | XRD |
|---|---|---|---|---|
| 41 | methyl ethyl ketone | 6 | r.t. | Form III |
| 42 | ethanol | 4 | r.t. | Form III |
| 43 | water | 1 | reflux | Form III |

TABLE 7-continued

| Example | Solvent | Volume (mL) | Temperature | XRD |
|---|---|---|---|---|
| 44 | ethanol-water (50:50) | 2 | r.t. | Form III |
| 45 | propyl acetate | 1 | reflux | Form III |
| 46 | ethyl acetate | 1 | reflux | Form III |

Example 47

Preparation of Lacosamide Crystalline Form IIII

This example illustrates a further process for preparing lacosamide crystalline Form III in accordance with the invention.

Lacosamide (150 mg) was dissolved in acetonitrile (1 mL) at reflux temperature. Then heptane (3 mL) was added. The mixture was allowed to cool to room temperature while stirring for 2 hours. The solid was filtered and analyzed by XRD.

Example 48

Preparation of Lacosamide Crystalline Form IV

This example illustrates a process for preparing lacosamide crystalline Form IV in accordance with the invention.

Lacosamide (150 mg) was dissolved in dichloromethane (1.5 mL) at room temperature. Then heptane (4 mL) was added. The mixture was stirred for 1 h at room temperature. The solid was filtered and analyzed by XRD.

The XRD of the lacosamide crystalline Form IV obtained is depicted in FIG. 9.

The IR of the lacosamide crystalline Form IV obtained is depicted in FIG. 10.

Example 49

Preparation of Lacosamide Crystalline Form I

Lacosamide (1.5 g) was dissolved in 2-propanol (5 mL) at reflux temperature. Then heptane (25 mL) was added. Some precipitate was observed when cooling the reaction mixture at about 87° C. The suspension was stirred at 80° C. for 30 minutes and then allowed to cool to room temperature. The solid was filtered, washed with 3 mL of heptane and dried at 40° C. under vacuum. 1.33 g of lacosamide was obtained (yield: 89%). The solid was analyzed by XRD.

Example 50

Preparation of Amorphous Lacosamide

This example illustrates a process for preparing amorphous Form lacosamide in accordance with the invention.

Lacosamide (150 mg) was dissolved in water (10 mL) at room temperature. The solution was evaporated to dryness in a rotary evaporator. The solid obtained was analyzed by XRD. The diffractogram is depicted in FIG. 12.

Examples 51-60

Preparation of Lacosamide as a Conglomerate

Crude lacosamide was crystallized from 10 volumes of ethyl acetate (ml solvent/g crude lacosamide).
The results are listed in Table 8.

TABLE 8

| | Enantiomeric purity (HPLC) of crude Lacosamide | | | Enantiomeric purity (HPLC) of Lacosamide after crystallization | | | |
|---|---|---|---|---|---|---|---|
| Example | (2S)-2-(acetylamino)-3-methoxy-N-(phenylmethyl) Propanamide (%) | (2R)-2-(acetylamino)-3-methoxy-N-(phenylmethyl) Propanamide (Lacosamide) % | e.e. (%) | ((2S)-2-(acetylamino)-3-methoxy-N-(phenylmethyl) Propanamide (%) | (2R)-2-(acetylamino)-3-methoxy-N-(phenylmethyl) propanamide (Lacosamide) % | e.e. (%) | Enantiomeric excess (e.e.) increase (%) |
| 51 | 23.79 | 76.21 | 52.42 | 16.62 | 83.38 | 66.76 | 14.34 |
| 52 | 19.07 | 80.93 | 61.86 | 11.87 | 88.13 | 76.26 | 14.40 |
| 53 | 16.98 | 83.02 | 66.04 | 2.28 | 97.72 | 95.44 | 29.40 |
| 54 | 16.97 | 83.04 | 66.07 | 2.73 | 97.27 | 94.54 | 28.47 |
| 55 | 15.75 | 84.25 | 68.50 | 2.05 | 97.95 | 95.90 | 27.40 |
| 56 | 12.58 | 87.42 | 74.84 | 3.40 | 96.61 | 93.21 | 18.37 |
| 57(a)[a] | 12.13 | 87.87 | 75.74 | 6.78 | 93.22 | 86.44 | 10.70 |
| 57(b)[a] | 6.78 | 93.22 | 86.44 | 0.76 | 99.24 | 98.48 | 12.04 |
| 58 | 5.05 | 94.95 | 89.90 | 0.22 | 99.78 | 99.56 | 9.66 |
| 59 | 3.93 | 96.07 | 92.14 | 0.11 | 99.89 | 99.78 | 7.64 |
| 60 | 1.95 | 98.05 | 96.11 | 0.17 | 99.83 | 99.66 | 3.55 |

[a]Crude lacosamide obtained in Example 57(a) was used as starting material for the example 57(b). Therefore, the crude lacosamide of Example 57(b) was crystallized twice.

For the resulting conglomerate mixtures as obtained further to the above mentioned Examples, lacosamide is present as a polymorphous mixture of crystalline Forms I and III (latter in trace amounts) in Example 53; a polymorphous mixture of crystalline Forms II and III (former in trace amounts) in Example 54; a polymorphous mixture of crystalline Forms I and III (latter in trace amounts) in Example 57(a); crystalline Form I in Example 57(b); crystalline Form I in Example 58; a polymorphous mixture of crystalline Forms I and II in Example 60.

Examples 61-62

Stability studies for Lacosamide Crystalline Form III

Samples corresponding to polymorphic Form III were stored under standard conditions (i.e. room temperature, normal pressure, air atmosphere). Samples were analyzed after some time by XRD. Results are summarized in Table 9.

TABLE 9

| Example | Sample | Storing time (days) | XRD |
| --- | --- | --- | --- |
| 61 | Example 41 | 295 | Form III |
| 62 | Example 42 | 290 | Form III |

Example 63

Stability Studies for Amorphous Lacosamide

Amorphous lacosamide as obtained in Example 50 was stored under standard conditions (i.e. room temperature, normal pressure, air atmosphere) for 304 days. Sample was then analyzed by XRD. FIG. 13 is the thus obtained XRD of amorphous lacosamide further to storage as above.

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A mixture of lacosamide enantiomers crystallized in a conglomerate Form, wherein said mixture of lacosamide enantiomers comprises a crystalline Form of lacosamide selected from the group consisting of lacosamide crystalline Form III characterized by an XRD pattern comprising peaks (2θ) at 6.5, 8.3, 10.3, 12.9, 15.6, 16.5, 17.5, 19.5, 21.2, 22.5, 24.2, 24.9, 27.0, and 28.5 degrees (±0.2 degrees); lacosamide crystalline Form I characterized by an XRD pattern comprising peaks (2θ) at 8.2, 10.3, 12.9, 15.6, 16.6, 17.6, 19.5, 20.8, 21.0, 21.4, 25.0, 25.3, 26.1, 27.2, 30.7, 31.4, and 36.6 degrees (±0.2 degrees); lacosamide crystalline Form II characterized by an XRD pattern comprising peaks (2θ) at 5.2, 6.6, 8.1, 10.6, 10.9, 12.5, 15.5, 16.1, 16.8, 17.4, 17.8, 20.5, 21.2, 21.5, 22.1, 22.5, 23.1, 23.8, 24.3, 25.7, 27.1, and 27.6 degrees (±0.2 degrees); lacosamide crystalline Form IV characterized by an XRD pattern comprising peaks (2θ) at 9.5, 14.3, 18.6, 20.0, 23.3 and 25.8 degrees (±0.2 degrees); and lacosamide crystalline Form T characterized by an XRD pattern comprising peaks (2θ) at 8.2, 12.9, 16.5, 19.5 and 24.8 degrees (±0.2 degrees); and mixtures of said crystalline Forms.

2. A process for separating enantiomers of lacosamide comprising conducting at least one direct crystallization of the mixture of claim 1.

3. A process for preparing enantiomerically enriched lacosamide, comprising providing a supersaturated solution of lacosamide, seeding the supersaturated solution of lacosamide with enantiomerically enriched lacosamide and recovering enantiomerically enriched lacosamide as a conglomerate, wherein the conglomerate comprises a crystalline Form of lacosamide selected from the group consisting of lacosamide crystalline Form III characterized by an XRD pattern comprising peaks (2θ) at 6.5, 8.3, 10.3, 12.9, 15.6, 16.5, 17.5, 19.5, 21.2, 22.5, 24.2, 24.9, 27.0, and 28.5 degrees (±0.2 degrees); lacosamide crystalline Form I characterized by an XRD pattern comprising peaks (2θ) at 8.2, 10.3, 12.9, 15.6, 16.6, 17.6, 19.5, 20.8, 21.0, 21.4, 25.0, 25.3, 26.1, 27.2, 30.7, 31.4, and 36.6 degrees (±0.2 degrees); lacosamide crystalline Form II characterized by an XRD pattern comprising peaks (2θ) at 5.2, 6.6, 8.1, 10.6, 10.9, 12.5, 15.5, 16.1. 16.8, 17.4, 17.8, 20.5, 21.2, 21.5, 22.1, 22.5, 23.1, 23.8, 24.3, 25.7, 27.1, and 27.6 degrees (±0.2 degrees); lacosamide crystalline Form IV characterized by an XRD pattern comprising peaks (2θ) at 9.5, 14.3, 18.6, 20.0, 23.3 and 25.8 degrees (±0.2 degrees); and lacosamide crystalline Form T characterized by an XRD pattern comprising peaks (2θ) at 8.2, 12.9, 16.5, 19.5 and 24.8 degrees (±0.2 degrees); and mixtures of said crystalline Forms.

4. A process for preparing enantiomerically enriched lacosamide, comprising providing a supersaturated solution of lacosamide comprising an epimerization agent, seeding the supersaturated solution of lacosamide with enantiomerically enriched lacosamide and recovering enantiomerically enriched lacosamide as a conglomerate, wherein the conglomerate comprises a crystalline Form of lacosamide selected from the group consisting of lacosamide crystalline Form III characterized by an XRD pattern comprising peaks (2θ) at 6.5, 8.3, 10.3, 12.9, 15.6, 16.5, 17.5, 19.5, 21.2, 22.5, 24.2, 24.9, 27.0, and 28.5 degrees (±0.2 degrees); lacosamide crystalline Form I characterized by an XRD pattern comprising peaks (2θ) at 8.2, 10.3, 12.9, 15.6, 16.6, 17.6, 19.5, 20.8, 21.0, 21.4, 25.0, 25.3, 26.1, 27.2, 30.7, 31.4, and 36.6 degrees (±0.2 degrees); lacosamide crystalline Form II characterized by an XRD pattern comprising peaks (2θ) at 5.2, 6.6, 8.1, 10.6, 10.9, 12.5, 15.5. 16.1, 16.8, 17.4, 17.8, 20.5, 21.2, 215, 22.1, 22.5, 23.1, 23.8, 24.3, 25.7, 27.1, and 27.6 degrees (±0.2 degrees); lacosamide crystalline Form IV characterized by an XRD pattern comprising peaks (2θ) at 9.5, 14.3, 18.6, 20.0, 23.3 and 25.8 degrees (±0.2 degrees); and lacosamide crystalline Form T characterized by an XRD pattern comprising peaks (2θ) at 8.2, 12,9, 16.5, 19.5 and 24.8 degrees (±0.2 degrees); and mixtures of said crystalline Forms.

5. The process according to claim 4, wherein said epimerization agent comprises a basic catalyst.

6. A process for preparing enantiomerically enriched lacosamide having an increased enantiomeric excess, comprising providing a solution of enantiomerically enriched lacosamide, conducting at least one direct crystallization of the solution comprising the enantiomerically enriched lacosamide and recovering enantiomerically enriched lacosamide having an increased enantiomeric excess as a conglomerate, wherein the conglomerate comprises a crystalline Form of lacosamide selected from the group consisting of lacosamide crystalline Form III characterized by an XRD pattern comprising peaks (2θ) at 6.5, 8.3, 10.3, 12.9, 15.6, 16.5, 17.5, 19.5, 21.2, 22.5, 24.2, 24.9, 27.0, and 28.5 degrees (±0.2 degrees); lacosamide crystalline Form I characterized by an XRD pattern comprising peaks (2θ) at 8.2 10.3, 12.9, 15.6, 16.6, 17.6, 19.5, 20.8, 21.0, 21.4, 25.0, 25.3, 26.1, 27.2 30.7, 31.4, and 36.6 degrees (±0.2 degrees); lacosamide crystalline Form II characterized by an XRD pattern comprising peaks (2θ) at 5.2, 6.6, 8.1, 10.6, 10.9, 12.5, 15.5, 16.1, 16.8, 17.4, 17.8, 20.5, 21.2, 21.5, 22.1, 22,5, 23,1, 23,8, 24.3, 25.7, 27.1, and 27.6 degrees (±0.2 degrees); lacosamide crystalline Form IV characterized by an XRD pattern comprising peaks (2θ) at 9.5, 14.3, 18.6, 20.0, 23.3 and 25.8 degrees (±0.2 degrees); and lacosamide crystalline Form T characterized by an XRD pattern comprising peaks (2θ) at 8.2, 12.9, 16.5, 19.5 and 24.8 degrees (±0.2 degrees): and mixtures of said crystalline Forms.

7. A process according to claim 2, wherein said lacosamide is lacosamide selected from the group consisting of crystalline Form III characterized by an XRD pattern comprising peaks (2θ) at 6.5, 8.3, 10.3, 12.9, 15.6, 16.5, 17.5, 19.5, 21.2, 22.5, 24.2, 24.9, 27.0, and 28.5 degrees (±0.2 degrees), lacosamide crystalline Form I characterized by an XRD pattern comprising peaks (2θ) at 8.2, 10.3, 12.9, 15.6, 16,6, 17.6, 19.5, 20.8, 21.0, 21.4, 25.0, 25.3, 26.1, 27.2, 30.7, 31.4, and 36.6 degrees (±0.2 degrees) and lacosamide crystalline Form II characterized by an XRD pattern comprising peaks (2θ) at 5.2, 6.6, 8.1, 10.6, 10.9, 12.5, 15.5, 16.1, 16.8, 17.4, 17.8, 20.5, 21.2, 21.5, 22.1, 22.5, 23.1, 23.8, 24.3, 25.7, 27.1, and 27.6 degrees (±0.2 degrees).

8. A process according to claim 3, wherein said lacosamide is lacosamide selected from the group consisting of crystalline Form III characterized by an XRD pattern comprising peaks (2θ) at 6.5, 8.3, 10.3, 12.9, 15.6, 16,5, 17.5, 19.5, 21.2, 22.5, 24.2, 24.9, 27.0, and 28.5 degrees (±0.2 degrees), lacosamide crystalline Form I characterized by an XRD pattern comprising peaks (2θ) at 8.2, 10.3, 12.9, 15.6, 16.6, 17.6, 19.5, 20.8, 21.0, 21.4, 25.0, 25.3, 26.1, 27.2, 30.7, 31.4, and 36.6 degrees (±0.2 degrees) and lacosamide crystalline Form II characterized by an XRD pattern comprising peaks (2θ) at 5.2, 6.6, 8.1, 10.6, 10.9, 12.5, 15.5, 16.1, 16.8, 17.4, 17.8, 20.5, 21.2, 21.5, 22.1, 22.5, 23.1, 23.8, 24.3, 25.7, 27.1, and 27.6 degrees (±0.2 degrees).

9. A process according to claim 4, wherein said lacosamide is lacosamide selected from the group consisting of crystalline Form III characterized by an XRD pattern comprising peaks (2θ) at 6.5, 8.3, 10.3, 12.9, 15.6, 16.5, 17.5, 19.5, 21.2, 22.5, 24.2, 24.9, 27.0, and 28.5 degrees (±0.2 degrees), lacosamide crystalline Form I characterized by an XRD pattern comprising peaks (2θ) at 8.2, 10.3, 12.9, 15.6, 16.6, 17.6, 19.5, 20.8, 21.0, 21.4, 25.0, 25.3, 26.1, 27.2, 30.7, 31.4, and 36.6 degrees (±0.2 degrees) and lacosamide crystalline Form II characterized by an XRD pattern comprising peaks (2θ) at 5.2, 6.6, 8.1, 10.6, 10.9, 12.5, 15.5, 16.1, 16.8, 17.4, 17.8, 20.5, 21.2, 21.5, 22.1, 22.5, 23.1, 23.8, 24.3, 25.7, 27.1, and 27.6 degrees (±0.2 degrees).

10. A process according to claim 6, wherein said lacosamide is lacosamide selected from the group consisting of crystalline Form III characterized by an XRD pattern comprising peaks (2θ) at 6.5, 8.3, 10.3, 12.9, 15.6, 16.5, 17.5, 19.5, 21.2, 22.5, 24.2, 24.9, 27.0, and 28.5 degrees (±0.2 degrees), lacosamide crystalline Form I characterized by an XRD pattern comprising peaks (2θ) at 8.2, 10.3, 12.9, 15.6, 16.6, 17.6, 19.5, 20.8, 21.0, 21.4, 25.0, 25.3, 26.1, 27.2, 30.7, 31.4, and 36.6 degrees (±0.2 degrees) and lacosamide crystalline Form II characterized by an XRD pattern comprising peaks (2θ) at 5.2, 6.6, 8.1, 10.6, 10.9, 12.5, 15.5, 16.1, 16.8, 17.4, 17.8, 20.5, 21.2, 21.5, 22.1, 22.5, 23.1, 23.8, 24.3, 25.7, 27.1, and 27.6 degrees (±0.2 degrees).

11. The process of claim 3, wherein the seed enantiomerically enriched lacosamide and the recovered enantiomerically enriched lacosamide are enriched with the (R)-enantiomer of lacosamide.

12. The process of claim 4, wherein the seed enantiomerically enriched lacosamide and the recovered enantiomerically enriched lacosamide are enriched with the (R)-enantiomer of lacosamide.

13. The process of claim 6, wherein the enantiomerically enriched lacosamide is enriched with the (R)-enantiomer of lacosamide.

14. The process of claim 11, wherein the recovered enantiomerically enriched lacosamide has an enantiomeric excess of at least 60%, as measured by percent area by HPLC.

15. The process of claim 12, wherein the recovered enantiomerically enriched lacosamide has an enantiomeric excess of at least 60%, as measured by percent area by HPLC.

16. The process of claim 13, wherein the enantiomerically enriched lacosamide has an enantiomeric excess of at least 60%, as measured by percent area by HPLC.

17. A mixture of lacosamide enantiomers crystallized in a conglomerate Form obtained by crystallization from ethyl acetate, wherein the conglomerate Form comprises a crystalline Form of lacosamide selected from the group consisting of lacosamide crystalline Form III characterized by an XRD pattern comprising peaks (2θ) at 6.5, 8.3, 10.3, 12.9, 15.6, 16.5, 17.5, 19.5, 21.2, 22.5, 24.2, 24.9, 27.0, and 28.5 degrees (±0.2 degrees); lacosamide crystalline Form I characterized by an XRD pattern comprising peaks (2θ) at 8.2, 10.3, 12.9, 15.6, 16.6, 17.6, 19.5, 20.8, 21.0, 21.4, 25.0, 25.3, 26.1, 27.2, 30.7, 31.4, and 36.6 degrees (±0.2 degrees); lacosamide crystalline Form II characterized by an XRD pattern comprising peaks (2θ) at 5.2, 6.6, 8.1, 10.6, 10.9, 12.5, 15.5, 16.1, 16.8, 17.4, 17.8, 20.5, 21.2, 21.5, 22.1, 22.5, 23.1, 23.8, 24.3, 25.7, 27.1, and 27.6 degrees (±0.2 degrees); lacosamide crystalline Form IV characterized by an XRD pattern comprising peaks (2θ) at 9.5, 14.3, 18.6, 20.0, 23.3 and 25.8 degrees (±0.2 degrees); and lacosamide crystalline Form T characterized by an XRD pattern comprising peaks (2θ) at 8.2, 12.9, 16.5, 19.5 and 24.8 degrees (±0.2 degrees); and mixtures of said crystalline Forms.

* * * * *